United States Patent
Kupershmidt et al.

(10) Patent No.: US 10,127,353 B2
(45) Date of Patent: Nov. 13, 2018

(54) METHOD AND SYSTEMS FOR QUERYING SEQUENCE-CENTRIC SCIENTIFIC INFORMATION

(71) Applicant: NextBio, Santa Clara, CA (US)

(72) Inventors: Ilya Kupershmidt, San Francisco, CA (US); Qiaojuan Jane Su, San Jose, CA (US)

(73) Assignee: Nextbio, San Diego, CA (US)

( * ) Notice: Subject to any disclaimer, the term of this patent is extended or adjusted under 35 U.S.C. 154(b) by 0 days.

(21) Appl. No.: 15/451,271

(22) Filed: Mar. 6, 2017

(65) Prior Publication Data

US 2017/0177793 A1  Jun. 22, 2017

Related U.S. Application Data

(63) Continuation of application No. 14/860,412, filed on Sep. 21, 2015, now Pat. No. 9,633,166, which is a
(Continued)

(51) Int. Cl.
*G06F 17/30* (2006.01)
*G06F 19/28* (2011.01)
(Continued)

(52) U.S. Cl.
CPC .......... *G06F 19/28* (2013.01); *G06F 17/3053* (2013.01); *G06F 17/30554* (2013.01);
(Continued)

(58) Field of Classification Search
CPC combination set(s) only.
See application file for complete search history.

(56) References Cited

U.S. PATENT DOCUMENTS 5,153,178 A  10/1992  Maroko
5,495,077 A  2/1996  Miller et al.
(Continued)

FOREIGN PATENT DOCUMENTS

JP  2002-528095 A  9/2002
JP  2004-152035 A  5/2004
(Continued)

OTHER PUBLICATIONS

Jiang, Daxin, Chun Tang, and Aidong Zhang. "Cluster analysis for gene expression data: A survey." IEEE Transactions on knowledge and data engineering 16, No. 11 (2004): 1370-1386.*
(Continued)

*Primary Examiner* — Farhan Syed
(74) *Attorney, Agent, or Firm* — Weaver Austin Villeneuve & Sampson LLP

(57) ABSTRACT

According to various embodiments, aspects of the invention provide a highly efficient meta-analysis infrastructure for performing research queries across a large number of studies and experiments from diverse sequencing technologies as well as different biological and chemical assays, data types and organisms, as well as systems to build and add to such an infrastructure. The methods, systems and apparatuses described enable combining orthogonal types of data and available public knowledge to elucidate mechanisms governing normal development, disease progression, as well as susceptibility of individuals to disease or response to drug treatments.

19 Claims, 23 Drawing Sheets

Related U.S. Application Data continuation of application No. 12/796,545, filed on Jun. 8, 2010, now Pat. No. 9,183,349, which is a continuation-in-part of application No. 11/641,539, filed on Dec. 18, 2006, now Pat. No. 8,275,737.

(60) Provisional application No. 61/185,926, filed on Jun. 10, 2009, provisional application No. 60/750,829, filed on Dec. 16, 2005.

(51) Int. Cl.
*G06F 19/18* (2011.01)
*G06F 19/22* (2011.01)
*G06F 19/24* (2011.01)

(52) U.S. Cl.
CPC .............. *G06F 19/18* (2013.01); *G06F 19/22* (2013.01); *G06F 19/24* (2013.01)

(56) References Cited

U.S. PATENT DOCUMENTS

| | | | |
|---|---|---|---|
| 6,122,636 A * | 9/2000 | Malloy | G06F 17/30595 |
| 6,151,601 A | 11/2000 | Papierniak et al. | |
| 6,185,561 B1 * | 2/2001 | Balaban | G06F 17/30893 |
| | | | 435/6.13 |
| 6,286,002 B1 | 9/2001 | Axaopoulos et al. | |
| 6,408,308 B1 * | 6/2002 | Maslyn | G06F 19/28 |
| | | | 435/287.2 |
| 6,465,183 B2 | 10/2002 | Wolber | |
| 6,580,910 B1 | 6/2003 | Mazur et al. | |
| 6,836,877 B1 | 12/2004 | Dupenloup | |
| 6,925,455 B2 | 8/2005 | Gong et al. | |
| 6,947,846 B2 | 9/2005 | Quake et al. | |
| 7,035,739 B2 | 4/2006 | Schadt et al. | |
| 7,072,665 B1 | 7/2006 | Blumberg et al. | |
| 7,103,519 B2 | 9/2006 | Singarajan et al. | |
| 7,155,453 B2 * | 12/2006 | Kincaid | G06F 17/30286 |
| | | | 707/770 |
| 7,225,183 B2 * | 5/2007 | Gardner | G06F 19/28 |
| 7,243,112 B2 * | 7/2007 | Qu | G06F 19/12 |
| 7,718,354 B2 * | 5/2010 | Ecker | C12Q 1/701 |
| | | | 435/5 |
| 7,761,392 B2 | 7/2010 | Mohamed et al. | |
| 7,798,401 B2 | 9/2010 | Jung et al. | |
| 7,930,172 B2 | 4/2011 | Bellegarda | |
| 8,071,309 B2 * | 12/2011 | Ecker | C12Q 1/689 |
| | | | 435/6.12 |
| 8,078,217 B2 | 12/2011 | Garcia | |
| 8,275,737 B2 | 9/2012 | Kupershmidt et al. | |
| 8,364,665 B2 | 1/2013 | Su et al. | |
| 8,655,817 B2 | 2/2014 | Hasey et al. | |
| 9,141,913 B2 | 9/2015 | Kupershmidt et al. | |
| 9,183,349 B2 | 11/2015 | Kupershmidt et al. | |
| 9,633,166 B2 | 4/2017 | Kupershmidt et al. | |
| 2001/0005852 A1 | 6/2001 | Bogle et al. | |
| 2001/0016314 A1 * | 8/2001 | Anderson | G01N 33/6803 |
| | | | 435/6.14 |
| 2002/0093591 A1 | 7/2002 | Gong et al. | |
| 2002/0137031 A1 | 9/2002 | Wolber | |
| 2002/0150966 A1 | 10/2002 | Muraca | |
| 2002/0159642 A1 | 10/2002 | Whitney | |
| 2002/0177138 A1 * | 11/2002 | Boissy | C12Q 1/68 |
| | | | 435/6.18 |
| 2002/0197632 A1 | 12/2002 | Moskowitz | |
| 2003/0055619 A1 | 3/2003 | Singarajan et al. | |
| 2003/0182281 A1 | 9/2003 | Wittkowski | |
| 2004/0071700 A1 | 4/2004 | Kim et al. | |
| 2004/0073955 A1 | 4/2004 | Chung | |
| 2004/0122708 A1 | 6/2004 | Avinash et al. | |
| 2004/0122790 A1 | 6/2004 | Walker et al. | |
| 2004/0162852 A1 * | 8/2004 | Qu | G06F 19/12 |
| 2004/0249791 A1 | 12/2004 | Waters et al. | |
| 2005/0081188 A1 | 4/2005 | Kumar et al. | |
| 2005/0196817 A1 | 9/2005 | Kingsmore et al. | |
| 2005/0216426 A1 | 9/2005 | Weston et al. | |
| 2006/0020399 A1 | 1/2006 | Shishiki | |
| 2006/0064415 A1 | 3/2006 | Guyon et al. | |
| 2006/0173828 A1 | 8/2006 | Rosenberg | |
| 2006/0253262 A1 * | 11/2006 | Ching | C12Q 1/6883 |
| | | | 702/20 |
| 2006/0277016 A1 | 12/2006 | Kouchi et al. | |
| 2006/0287106 A1 | 12/2006 | Jensen | |
| 2007/0038867 A1 | 2/2007 | Verbauwhede et al. | |
| 2007/0118399 A1 | 5/2007 | Avinash et al. | |
| 2007/0156692 A1 | 7/2007 | Rosewarne | |
| 2007/0162411 A1 | 7/2007 | Kupershmidt et al. | |
| 2008/0075789 A1 | 3/2008 | Vawter et al. | |
| 2008/0103995 A1 | 5/2008 | Mohamed et al. | |
| 2008/0144124 A1 | 6/2008 | Samadani et al. | |
| 2008/0147451 A1 | 6/2008 | Schnack | |
| 2008/0155018 A1 | 6/2008 | Fortier et al. | |
| 2009/0041862 A1 * | 2/2009 | Schofield | C12N 9/12 |
| | | | 424/722 |
| 2009/0049019 A1 | 2/2009 | Su et al. | |
| 2009/0222400 A1 | 9/2009 | Kupershmidt et al. | |
| 2009/0238465 A1 | 9/2009 | Lee et al. | |
| 2010/0115421 A1 * | 5/2010 | Bejjani | G06F 15/16 |
| | | | 715/751 |
| 2010/0172567 A1 | 7/2010 | Prokoski | |
| 2010/0277650 A1 | 11/2010 | Matsuzaki | |
| 2010/0279423 A1 | 11/2010 | Brennan et al. | |
| 2010/0305806 A1 | 12/2010 | Hawley | |
| 2010/0318528 A1 | 12/2010 | Kupershmidt et al. | |
| 2011/0119209 A1 | 5/2011 | Kirshenbaum et al. | |
| 2011/0179066 A1 * | 7/2011 | Cardno | G06F 17/30 |
| | | | 707/769 |
| 2011/0263445 A1 | 10/2011 | Wolber | |
| 2013/0144916 A1 * | 6/2013 | Lum | G06F 19/24 |
| | | | 707/790 |
| 2013/0166320 A1 | 6/2013 | Kupershmidt et al. | |
| 2013/0166599 A1 | 6/2013 | Kupershmidt et al. | |
| 2015/0193576 A9 | 7/2015 | Kupershmidt et al. | |
| 2016/0132641 A1 | 5/2016 | Kupershmidt et al. | |
| 2016/0232224 A1 | 8/2016 | Kupershmidt et al. | |

FOREIGN PATENT DOCUMENTS

| | | |
|---|---|---|
| JP | 2004-535612 A | 11/2004 |
| JP | 2005-518793 A | 6/2005 |
| JP | 2005-309836 A | 11/2005 |
| JP | 2009-520278 A | 5/2009 |
| WO | WO 2000/024936 | 5/2000 |
| WO | WO 2001/055951 | 8/2001 |
| WO | WO 2007/075488 | 7/2007 |
| WO | WO 2009/039425 | 3/2009 |
| WO | WO 2009/111581 | 9/2009 |

OTHER PUBLICATIONS

U.S. Office Action dated Sep. 29, 2010, issued in U.S. Appl. No. 11/641,539.
U.S. Final Office Action dated May 11, 2011, issued in U.S. Appl. No. 11/641,539.
U.S. Notice of Allowance dated Jul. 19, 2012, issued in U.S. Appl. No. 11/641,539.
U.S. Office Action dated Jun. 23, 2015, issued in U.S. Appl. No. 13/588,526.
U.S. Final Office Action dated Dec. 16, 2015, issued in U.S. Appl. No. 13/588,526.
U.S. Advisory Action and Examiner initiated interview summary dated Mar. 2, 2016 issued in U.S. Appl. No. 13/588,526.
U.S. Office Action dated Jun. 14, 2016, issued in U.S. Appl. No. 13/588,526.
U.S. Office Action dated Feb. 9, 2017, issued in U.S. Appl. No. 13/588,526.
U.S. Office Action dated Dec. 22, 2010, issued in U.S. Appl. No. 12/234,435.
U.S. Final Office Action dated Jul. 28, 2011 issued in U.S. Appl. No. 12/234,435.

(56) References Cited

OTHER PUBLICATIONS

U.S. Notice of Allowance dated Sep. 28, 2012, issued in U.S. Appl. No. 12/234,435.
U.S. Office Action dated Jan. 24, 2012 issued in U.S. Appl. No. 12/398,107.
U.S. Final Office Action dated Oct. 5, 2012, issued in U.S. Appl. No. 12/398,107.
U.S. Office Action dated Aug. 15, 2014, issued in U.S. Appl. No. 12/398,107.
U.S. Final Office Action dated Mar. 13, 2015, issued in U.S. Appl. No. 12/398,107.
U.S. Notice of Allowance dated Jul. 31, 2015, issued in U.S. Appl. No. 12/398,107.
U.S. Office Action dated Feb. 24, 2017, issued in U.S. Appl. No. 14/828,378.
U.S. Office Action dated Jan. 26, 2012, issued in U.S. Appl. No. 12/796,545.
U.S. Final Office Action dated Oct. 12, 2012, issued in U.S. Appl. No. 12/796,545.
U.S. Office Action dated Sep. 23, 2013, issued in U.S. Appl. No. 12/796,545.
U.S. Office Action dated Jul. 9, 2014, issued in U.S. Appl. No. 12/796,545.
U.S. Office Action dated Mar. 12, 2015, issued in U.S. Appl. No. 12/796,545.
U.S. Notice of Allowance dated Aug. 19, 2015, issued in U.S. Appl. No. 12/796,545.
U.S. Office Action dated Jul. 28, 2016, issued in U.S. Appl. No. 14/860,412.
U.S. Notice of Allowance dated Dec. 5, 2016, issued in U.S. Appl. No. 14/860,412.
U.S. Office Action dated Oct. 10, 2013, issued in U.S. Appl. No. 13/621,756.
U.S. Office Action dated Jul. 29, 2014, issued in U.S. Appl. No. 13/621,756.
U.S. Final Office Action dated Feb. 12, 2015, issued in U.S. Appl. No. 13/621,756.
U.S. Office Action dated Jun. 3, 2015, issued in U.S. Appl. No. 13/621,756.
U.S. Final Office Action dated Dec. 17, 2015, issued in U.S. Appl. No. 13/621,756.
PCT International Search Report and Written Opinion dated Mar. 20, 2008, issued in PCT/US 2006/048067.
PCT International Preliminary Report on Patentability dated Jun. 18, 2008, issued in PCT/US 2006/048067.
European Supplemental Search Report dated Mar. 23, 2012, issued in EP 06 84 7688.6.
Japanese Office Action dated May 22, 2012, issued in JP 2008-545870.
PCT International Search Report and Written Opinion dated Dec. 4, 2008, issued in PCT/US08/77097.
PCT International Preliminary Report on Patentability dated Mar. 24, 2010, issued in PCT/US08/77097.
PCT International Search Report and Written Opinion dated May 6, 2009 issued in PCT/US06/36058.
PCT International Preliminary Report on Patentability dated Sep. 7, 2010, issued in PCT/US06/36058.

Barad, et al. (2004) "MicroRNA expression detected by oligonucleotide microarrays: System establishment and expression profiling in human tissues" *Genome Research*, 14:2486-2494.
Barrett, T., et al., (2005) "NCBI GEO: Mining Millions of Expression Profiles—Database and Tools," *Nucleic Acids Research*, Database Issue, 33:D562-0566.
Brown, et al. (2000) "Knowledge-based analysis of microarray gene expression data by using support vector machines" *PNAS*, 97(1): 262-267.
De La Vega, et al. (2005) "Assessment of two flexible and compatible SNP genotyping platforms: TaqMan® SNP Genotyping Assays and the SNPlex TM Genotyping System," *Mutation Research/Fundamental and Molecular Mechanisms of Mutagenesis*, 573(1):111-135.
Dooley, et al. (2003) "Biomarkers of human cutaneous squamous cell carcinoma from tissues and cell lines identified by DNA microarrays and qRT-PCR," *Biochemical and Biophysical Research Communications* 306:1026-1036.
Engreit, et al., (2011) "ProfileChaser: searching microarray repositories based on genome-wide patterns of differential expression," *BIOINFORMATICS*, 27(23):3317-3318.
Ganter, et al. (2005) "Development of a large-scale chemogenomics database to improve drug candidate selection and to understand mechanisms of chemical toxicity and action," *Journal of Biotechnology*, 119:219-244.
Jiang, et al. (Nov. 204) "Cluster Analysis for Gene Expression Data: A Survey" *IEEE Transactions on Knowledge and Data Engineering*, 16(11):1370-1386.
Kupershmidt, et al., (Sep. 2010) "Ontology-Based Meta-Analysis of Global Collections of High-Throughput Public Data," *PLOS ONE*, 5(9): 1-13.
Lamb, et al., (2006) "The Connectivity Map: using gene-expression signatures to connect small molecules, genes, and disease," *Science*, 313:1929-1935.
Liu, W., et al. (Jun. 1, 2001) "Rank-Based Algorithms for Analysis of Microarrays," *Proceedings of SPIE*, US, 4266:56-67.
Raja, Alexandra, "Querying Microarray Databases," Masters Thesis, University of Texas, Published Dec. 2005, retrieved by Foreign Examiner on Apr. 21, 2009, Retrieved from the Internet: <URL:https://dspace.uta.edu/bitstream/10106/251/1/umi-uta-1117.pdf>, 163 pages.
Rashef, et al., (2011) "Detecting Novel Associations in Large Data Sets," *Science*, 334:1518-1524.
Shah, S. P., et al., (Feb. 21, 2005) "Atlas—a Data Warehouse for Integrative Bioinformatics," London GB, 6(34):1-16.
Wu, et al., (2009) "BioGPS: an extensible and customizable portal for querying and organizing gene annotation resources," *Genome Biol.*, 10(11):R130, 12 pages.
U.S. Final Office Action dated Sep. 21, 2017, issued in U.S. Appl. No. 14/828,378.
U.S. Final Office Action dated Oct. 4, 2017, issued in U.S. Appl. No. 13/588,526.
U.S. Appl. No. 11/640,121, filed Dec. 15, 2006, Su et al.
U.S. Appl. No. 13/621,736, filed Sep. 17, 2012, Kupershmidt et al.
U.S. Office Action dated Apr. 6, 2018 issued in U.S. Appl. No. 13/588,526.
U.S. Office Action dated Apr. 19, 2018 issued in U.S. Appl. No. 14/828,378.

\* cited by examiner

Platform SNP Data –
Aggregate
Genotyping 321　　　　325　　323

| # Marker ID | Marker Type | P-value (Genotypic association) | Allele 1 | Allele 2 | Chr ID | Chr Position | Submitted SNP ID | ss2rs | rs2genome | G11 count (case) |
|---|---|---|---|---|---|---|---|---|---|---|
| rs2977670 | SNP | 0.07243 | G | C | 1 | 713754 | ss65798767 | + | | 237 |
| rs7526509 | SNP | 0.1589 | T | A | 1 | 988737 | ss65739685 | + | | 0 |
| rs3934834 | SNP | 0.4863 | T | C | 1 | 995669 | ss66715090 | + | | 7 |
| rs3766193 | SNP | 0.8232 | C | G | 1 | 1007033 | ss65723133 | + | | 77 |
| rs12096277 | SNP | 0.556 | A | G | 1 | 1007461 | ss65745697 | + | | 268 |
| rs3737728 | SNP | 0.5198 | T | C | 1 | 1011278 | ss66681235 | + | | 14 |
| rs6687776 | SNP | 0.9318 | T | C | 1 | 1020428 | ss66623403 | + | | 8 |
| rs6678318 | SNP | 0.8867 | A | G | 1 | 1020496 | ss65819753 | + | | 8 |
| rs9651273 | SNP | 0.1288 | A | G | 1 | 1021403 | ss66791550 | + | | 14 |
| rs4970405 | SNP | 0.9583 | A | G | 1 | 1038818 | ss66562029 | + | | 212 |
| rs12726255 | SNP | 0.872 | A | G | 1 | 1039813 | ss66637559 | + | | 200 |
| rs7548798 | SNP | 0.1841 | T | C | 1 | 1050037 | ss65820363 | + | | 17 |
| rs2298217 | SNP | 0.1646 | T | C | 1 | 1054842 | ss66677402 | + | | 13 |
| rs4970357 | SNP | 0.87 | A | C | 1 | 1066927 | ss66620776 | + | | 220 |
| rs11260603 | SNP | 0.2252 | T | C | 1 | 1069061 | ss65736876 | + | | 160 |

Figure 3C

Platform SNP Data –
Arbitrary SNP list 331　　333

| # Marker ID | P-value (Genotypic association) |
|---|---|
| rs2977670 | 0.07243 |
| rs7526509 | 0.1589 |
| rs3934834 | 0.4863 |
| rs3766193 | 0.8232 |
| rs12096277 | 0.556 |
| rs3737728 | 0.5198 |
| rs6687776 | 0.9318 |
| rs6678318 | 0.8867 |
| rs9651273 | 0.1288 |
| rs4970405 | 0.9583 |
| rs12726255 | 0.872 |
| rs7548798 | 0.1841 |
| rs2298217 | 0.1646 |
| rs4970357 | 0.87 |
| rs11260603 | 0.2252 |

Figure 3D

SR Data –
Methylation

| chromosome | start | stop | num.mark | seg.mean |
|---|---|---|---|---|
| 1 | 554267 | 72533855 | 6384 | 0.0456 |
| 1 | 72550247 | 72568008 | 2 | 1.2471 |
| 1 | 72602596 | 74674719 | 93 | 0.0994 |
| 1 | 74693651 | 74877529 | 20 | -0.3621 |
| 1 | 74885003 | 74952060 | 7 | -0.6845 |
| 1 | 74961517 | 75110250 | 10 | -0.3235 |
| 1 | 75148401 | 116948645 | 3057 | 0.0836 |
| 1 | 116950995 | 117008722 | 5 | -0.4321 |
| 1 | 117014630 | 150816179 | 803 | 0.0395 |
| 1 | 150823072 | 150848508 | 4 | -1.5222 |
| 1 | 150857069 | 247185355 | 8108 | 0.0432 |
| 10 | 126360 | 135286022 | 10779 | -0.1383 |
| 11 | 192957 | 54789836 | 3966 | -0.1952 |
| 11 | 54807282 | 55118213 | 32 | 0.1272 |

Figure 3E

SR Data – ChiP-Seq

| Chr | Hit Start | Hit End | Sample Read Counts | Input Read Counts | Ratio | Excess |
|---|---|---|---|---|---|---|
| chr13 | 267673 | 268430 | 2910 | 22 | 134.439309172379 | 2888 |
| chr11 | 439299 | 440251 | 2443 | 59 | 41.4870967318513 | 2384 |
| chr8 | 105260 | 105958 | 1942 | 32 | 62.0402291726651 | 1910 |
| chr1 | 151009 | 151977 | 1877 | 34 | 55.6486977364312 | 1843 |
| chr4 | 449433 | 450096 | 1729 | 23 | 75.2067495290997 | 1706 |
| chr10 | 435378 | 436976 | 1820 | 142 | 12.8641877426043 | 1678 |
| chr14 | 628459 | 629279 | 1662 | 46 | 36.6752449810713 | 1616 |
| chr5 | 151706 | 152461 | 1509 | 30 | 50.59159598763 | 1479 |
| chr15 | 326302 | 327049 | 1196 | 23 | 52.0856925974972 | 1173 |
| chr6 | 148071 | 148925 | 1149 | 27 | 43.8298298548037 | 1122 |
| chr12 | 150542 | 151443 | 1171 | 64 | 18.4706925451619 | 1107 |
| chr16 | 555708 | 556341 | 1122 | 20 | 56.422423233896 | 1102 |

Figure 3F

Mapping features from
SNP Platform data

Mapping features from
Sequence Region data

| | In Feature Set F2 | Not In Feature Set F2 | Totals |
|---|---|---|---|
| Mapped to Feature Set F1 | F1∩F2 | F1∩P2 - F1∩F2 | F1∩P2 |
| Not Mapped to Feature Set F1 | F2∩P1-F1∩B2 | P1∩P2-F1∩P2-F2∩P1+F1∩F2 | P1∩P2 - F1∩P2 |
| Totals | F2∩P1 | P1∩P2- F2∩P1 | P1∩P2 |

METHOD AND SYSTEMS FOR QUERYING SEQUENCE-CENTRIC SCIENTIFIC INFORMATION

CROSS REFERENCE TO RELATED APPLICATION

This application claims priority as a continuation application under 35 U.S.C. 120 to U.S. patent application Ser. No. 14/860,412, titled "SEQUENCE-CENTRIC SCIENTIFIC INFORMATION MANAGEMENT," filed Sep. 21, 2015, which claims priority as a continuation application under 35 U.S.C. 120 to U.S. patent application Ser. No. 12/796,545, titled "SEQUENCE-CENTRIC SCIENTIFIC INFORMATION MANAGEMENT," filed Jun. 8, 2010, which claims the benefit under 35 U.S.C. 119(e) to U.S. Provisional Application No. 61/185,926, titled "SEQUENCE-CENTRIC SCIENTIFIC INFORMATION MANAGEMENT," filed Jun. 10, 2009; U.S. patent application Ser. No. 12/796,545 also claims priority as a continuation-in-part under 35 U.S.C. 120 to U.S. patent application Ser. No. 11/641,539, filed Dec. 18, 2006, titled "SYSTEM AND METHOD FOR SCIENTIFIC INFORMATION KNOWLEDGE MANAGEMENT", which claims the benefit under 35 U.S.C. 119(e) to U.S. Provisional Application No. 60/750,829, filed Dec. 16, 2005; all of the above applications are herein incorporated by reference in their entireties.

BACKGROUND OF THE INVENTION

The present invention relates generally to methods, systems and apparatus for storing and retrieving biological, chemical and medical information. Research in these fields has increasingly shifted from the laboratory bench to the computer-based methods. Public sources such as NCBI (National Center for Biotechnology Information), for example, provide databases with genetic and molecular data. Between these and private sources, an enormous amount of data is available to the researcher from various assay platforms, organisms, data types, etc. As the amount of biomedical information disseminated grows, researchers need fast and efficient tools to quickly assimilate new information and integrate it with pre-existing information across different platforms, organisms, etc. Researchers also need tools to quickly navigate through and analyze diverse types of information.

SUMMARY OF THE INVENTION

According to various embodiments, aspects of the invention provide a highly efficient meta-analysis infrastructure for performing research queries across a large number of studies and experiments from diverse sequencing technologies as well as different biological and chemical assays, data types and organisms, as well as systems to build and add to such an infrastructure. The methods, systems and apparatuses described enable combining orthogonal types of data and available public knowledge to elucidate mechanisms governing normal development, disease progression, as well as susceptibility of individuals to disease or response to drug treatments. For example, multi-dimensional data sets from mutation, methylation, chromosomal copy-number aberration analysis and gene expression profiling may be combined and used to elucidate core pathways driving tumor or disease development and its resistance to therapy.

BRIEF DESCRIPTION OF THE DRAWINGS

FIG. 3C presents an example of platform SNP aggregate data.

FIG. 3D presents another example of a SNP platform data file, in this case an arbitrary list of features (SNPs) as identified by identification numbers.

FIGS. 3E and 3F each show example sequence/platform sequence region (SR) data files.

DETAILED DESCRIPTION OF SPECIFIC EMBODIMENTS

1. Introduction and Relevant Terminology

Figure 1:
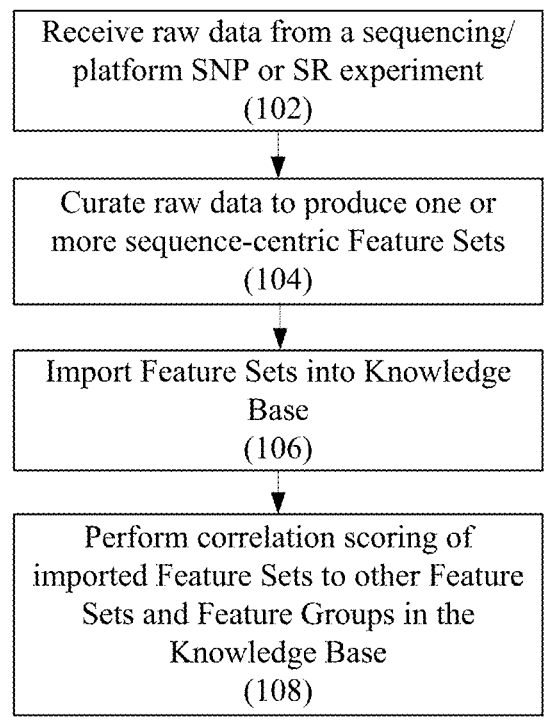
FIG. 1 presents an overview of a process of integrating sequence-centric information into a knowledge base according to various embodiments.

The present invention relates to methods, systems and apparatus for querying and interpreting data produced by next-generation sequencing technologies. The methods, systems and apparatus described herein support diverse scientific and medial applications, including studies on DNA methylation, protein-DNA interactions, transcriptomics, and comparative sequence analysis.

According to various embodiments, aspects of the invention provide a highly efficient meta-analysis infrastructure for performing research queries across a large number of studies and experiments from diverse sequencing technologies as well as different biological and chemical assays, data types and organisms, as well as systems to build and add to such an infrastructure. The methods, systems and apparatuses described enable combining orthogonal types of data and available public knowledge to elucidate mechanisms governing normal development, disease progression, as well as susceptibility of individuals to disease or response to drug treatments. For example, multi-dimensional data sets from mutation, methylation, chromosomal copy-number aberration analysis and gene expression profiling may be combined and used to elucidate core pathways driving tumor or disease development and its resistance to therapy.

Data from individual sequencing studies may be correlated with other orthogonal data and public information. As more of this data becomes publicly available it can be correlated with previous findings on relevant genes, genomic regions and phenotypes. For example, comparing epigenetic patterns with legacy microarray studies for a given phenotype can provide valuable scientific insights into importance of certain genes and mechanism of their regulation. Understanding the function of de novo SNPs can be gleaned from other data exploring nearby or correlated SNPs and genomic regions within the context of a given phenotype.

Commercial organizations, academic consortiums and individual laboratories that have accumulated legacy data from other mainstream technologies such as microarrays may turn this combined information into a new knowledge discovery resource. A sequence-centric framework for incorporating data from next-generation sequence-centric studies is provided, including integration with gene-centric data. The sequence-centric framework enables researchers to integrate their sequence-centric based data sets, and correlate them with previous sequence-centric and gene-centric data to identify important connections between diverse phenotypes at the level of genomic variations, rearrangements, epigenetic modifications, and gene and protein expression patterns.

While most of the description below is presented in terms of systems, methods and apparatuses that integrate and allow exploration of data from genetic based platforms and studies, the invention is by no means so limited. For example, the invention covers chemical and clinical data. The invention is also not limited to the specific examples of integrating and interpreting sequence-centric data presented below. In the following description, numerous specific details are set forth in order to provide a thorough understanding of the present invention. It will be apparent, however, that the present invention may be practiced without limitation to some of the specific details presented herein. For example, one of skill in the art will understand that various modifications and optimizations of the methods described herein may be made without departing from the scope of the invention, including performing operations in different orders or with different parameters, adding or removing various operations, etc.

The following terms are used throughout the specification. The descriptions are provided to assist in understanding the specification, but do not necessarily limit the scope of the invention.

Raw data—This is the data from one or more experiments that provides information about one or more samples. Examples of platforms used to produce raw data include, but are not limited to, microarray platforms including RNA and miRNA expression, SNP genotyping, protein expression, protein-DNA interaction and methylation data and amplification/deletion of chromosomal regions platforms, quantitative polymerase chain reaction (QPCR) gene expression platforms, identified novel genetic variants, copy-number variation (CNV) detection platforms, detecting chromosomal aberrations (amplifications/deletions) and whole genome sequencing. While the description below chiefly concerns genetic sequence-centric raw data, the methods described may be extrapolated to other types of sequence-centric data, e.g., protein sequences. In addition, the methods and systems described herein may include information derived from other raw data sources as well as deriving data from other raw data sources.

In certain embodiments, raw data is not yet processed to a point suitable for use in the databases and systems of this invention. Subsequent manipulation reduces it to the form of one or more "feature sets" suitable for use in such databases and systems. The process of converting the raw data to feature sets is sometimes referred to as curation.

Certain examples presented herein concern biological experiments in which a stimulus acts on a biological sample such as a tissue or cell culture. Often the biological experiment will have associated clinical parameters such as tumor stage, patient history, etc. The invention is not however limited to biological samples and may involve, for example, experiments on non-biological samples such as chemical compounds, various types of synthetic and natural materials, etc. and their effects on various types of assays (e.g., cancer cell line progression).

Whether working with biological or non-biological samples, the sample may be exposed to one or more stimuli or treatments to produce test data. Control data may also be produced. The stimulus is chosen as appropriate for the particular study undertaken. Examples of stimuli that may be employed are exposure to particular materials or compositions, radiation (including all manner of electromagnetic and particle radiation), forces (including mechanical (e.g., gravitational), electrical, magnetic, and nuclear), fields, thermal energy, and the like. General examples of materials that may be used as stimuli include organic and inorganic chemical compounds, biological materials such as nucleic acids, carbohydrates, proteins and peptides, lipids, various infectious agents, mixtures of the foregoing, and the like. Other general examples of stimuli include non-ambient temperature, non-ambient pressure, acoustic energy, electromagnetic radiation of all frequencies, the lack of a particular material (e.g., the lack of oxygen as in ischemia), temporal factors, etc. As suggested, a particularly important class of stimuli in the context of this invention is exposure to therapeutic agents (including agents suspected of being therapeutic but not yet proven to have this property). Often the therapeutic agent is a chemical compound such as a drug or drug candidate or a compound present in the environment. The biological impact of chemical compounds is manifest as a change in a feature such as a level of gene expression or a phenotypic characteristic.

As suggested, the raw data will include "features" for which relevant information is produced from the experiment. In many examples the features are genes or genetic information from a particular tissue or cell sample exposed to a particular stimulus. In other examples the features are sequence regions.

A typical biological experiment determines expression or other information about a gene or other feature associated with a particular cell type or tissue type. Other types of genetic features for which experimental information may be collected in raw data include SNP patterns (e.g., haplotype blocks), portions of genes (e.g., exons/introns or regulatory motifs), regions of a genome or chromosome spanning more than one gene, etc. Other types of biological features include phenotypic features such as the morphology of cells and cellular organelles such as nuclei, Golgi, etc. Types of chemical features include compounds, metabolites, etc.

The raw data may be generated from any of various types of experiments using various types of platforms (e.g., any of a number of microarray systems including gene microarrays, SNP microarrays and protein microarrays, cell counting systems, High-Throughput Screening ("HTS") platforms, etc.). For example, an oligonucleotide microarray is also used in experiments to determine expression of multiple genes in a particular cell type of a particular organism. In another example, mass spectrometry is used to determine abundance of proteins in samples. In certain embodiments, raw data includes genetic information about an individual or a population.

Feature set—This refers to a data set derived from the "raw data" taken from one or more experiments on one or more samples. In certain embodiments, the feature set includes one or more features (typically a plurality of features) and associated information about the impact of the experiment(s) on those features. At some point, the features of a feature set may be ranked (at least temporarily) based on their relative levels of response to the stimulus or treatment in the experiment(s) or based on their magnitude and direction of change between different phenotypes, as well as their ability to differentiate different phenotypic states (e.g., late tumor stage versus early tumor stage).

For reasons of storage and computational efficiency, for example, the feature set may include information about only a subset of the features or responses contained in the raw data. As indicated, a process such as curation converts raw data to feature sets.

In certain embodiments, the feature set pertains to raw data associated with a particular question or issue (e.g., does a particular chemical compound interact with proteins in a particular pathway). Depending on the raw data and the study, the feature set may be limited to a single cell type of a single organism. From the perspective of a "Directory," a feature set belongs to a "Study." In other words, a single study may include one or more feature sets.

In many embodiments, the feature set is either a "bioset" or a "chemset." A bioset typically contains data providing information about the biological impact of a particular stimulus or treatment. The features of a bioset are typically units of genetic or phenotypic information as presented above. These are ranked based on their level of response to the stimulus (e.g., a degree of up or down regulation in expression), or based on their magnitude and direction of change between different phenotypes, as well as their ability to differentiate different phenotypic states (e.g., late tumor stage versus early tumor stage). A chemset typically contains data about a panel of chemical compounds and how they interact with a sample, such as a biological sample. The features of a chemset are typically individual chemical compounds or concentrations of particular chemical compounds. The associated information about these features may be EC50 values, IC50 values, or the like.

A feature set typically includes, in addition to the identities of one or more features, statistical information about each feature and possibly common names or other information about each feature. A feature set may include still other pieces of information for each feature such as associated description of key features, user-based annotations, etc. The statistical information may include p-values of data for features (from the data curation stage), "fold change" data, and the like. A fold change indicates the number of times (fold) that expression is increased or decreased in the test or control experiment (e.g., a particular gene's expression increased "4-fold" in response to a treatment). A feature set may also contain features that represent a "normal state", rather than an indication of change. For example, a feature set may contain a set of genes that have "normal and uniform" expression levels across a majority of human tissues. In this case, the feature set would not necessarily indicate change, but rather a lack thereof.

In certain embodiments, a rank is ascribed to each feature, at least temporarily. This may be simply a measure of relative response within the group of features in the feature set. As an example, the rank may be a measure of the relative difference in expression (up or down regulation) between the features of a control and a test experiment. In certain embodiments, the rank is independent of the absolute value of the feature response. Thus, for example, one feature set may have a feature ranked number two that has a 1.5 fold increase in response, while a different feature set has the same feature ranked number ten that has a 5 fold increase in response to a different stimulus.

Directional feature set—A directional feature set is a feature set that contains information about the direction of change in a feature relative to a control. Bi-directional feature sets, for example, contain information about which features are up-regulated and which features are down-regulated in response to a control. One example of a bi-directional feature set is a gene expression profile that contains information about up and down regulated genes in a particular disease state relative to normal state, or in a treated sample relative to non-treated. As used herein, the terms "up-regulated" and "down-regulated" and similar terms are not limited to gene or protein expression, but include any differential impact or response of a feature. Examples include, but are not limited to, biological impact of chemical compounds or other stimulus as manifested as a change in a feature such as a level of gene expression or a phenotypic characteristic.

Non-directional feature sets contain features without indication of a direction of change of that feature. This includes gene expression, as well as different biological measurements in which some type of biological response is measured. For example, a non-directional feature set may contain genes that are changed in response to a stimulus, without an indication of the direction (up or down) of that change. The non-directional feature set may contain only up-regulated features, only down-regulated features, or both up and down-regulated features, but without indication of the direction of the change, so that all features are considered based on the magnitude of change only.

Gene-centric feature set—These are data sets in which the features are genes or proteins, e.g., as generated from platforms such as gene expression microarrays and proteomics platforms.

Sequence-centric feature set—These data sets include genomic sequence information and typically associated statistics and/or non-numerical information. Two main categories of features in sequence-centric feature sets are sequence or genomic regions and SNPs. SNPs may be thought of as a special case of a sequence region. Certain sequence-centric feature sets may contain information about the genetic profile or other molecular profiling data from an individual's sample (either genome wide or targeted). Unlike other feature sets, these "individual" feature sets often do not contain statistical information associated with the features but allele calls (sequencing for the sample). In certain embodiments, features in these individual features sets are not ranked and these individual feature sets are not correlated with all other feature sets during pre-processing. Certain feature sets contain aggregate data from multiple patient samples or other data sources such as plants, etc.

Feature group—This refers to a group of features (e.g., genes) related to one another. As an example, the members of a feature group may all belong to the same protein pathway in a particular cell or they may share a common function or a common structural feature. A feature group may also group compounds based on their mechanism of action or their structural/binding features.

Index set—The index set is a set in the knowledge base that contains feature identifiers and mapping identifiers and is used to map all features of the feature sets imported to feature sets and feature groups already in the knowledge base. For example, the index set may contain several million feature identifiers pointing to several hundred thousand mapping identifiers. Each mapping identifier (in some instances, also referred to as an address) represents a unique feature, e.g., a unique gene in the mouse genome. In certain embodiments, the index set may contain diverse types of feature identifiers (e.g., genes, genetic regions, etc.), each having a pointer to a unique identifier or address. The index set may be added to or changed as new knowledge is acquired.

Knowledge base—This refers to a collection of data used to analyze and respond to queries. In certain embodiments, it includes one or more feature sets, feature groups, and metadata for organizing the feature sets in a particular hierarchy or directory (e.g., a hierarchy of studies and projects). In addition, a knowledge base may include information correlating feature sets to one another and to feature groups, a list of globally unique terms or identifiers for genes or other features, such as lists of features measured on different platforms (e.g., Affymetrix human HG_U133A chip), total number of features in different organisms, their corresponding transcripts, protein products and their relationships. A knowledge base typically also contains a taxonomy that contains a list of all tags (keywords) for different tissues, disease states, compound types, phenotypes, cells, as well as their relationships. For example, taxonomy defines relationships between cancer and liver cancer, and also contains keywords associated with each of these groups (e.g., a keyword "neoplasm" has the same meaning as "cancer"). Typically, though not necessarily, at least some of the data in the knowledge base is organized in a database.

Curation—Curation is the process of converting raw data to one or more feature sets (or feature groups). In some cases, it greatly reduces the amount of data contained in the raw data from an experiment. It removes the data for features that do not have significance. In certain embodiments, this means that features that do not increase or decrease significantly in expression between the control and test experiments are not included in the feature sets. The process of curation identifies such features and removes them from the raw data. The curation process also identifies relevant clinical questions in the raw data that are used to define feature sets. Curation also provides the feature set in an appropriate standardized format for use in the knowledge base.

Data import—Data import is the process of bringing feature sets and feature groups into a knowledge base or other repository in the system, and is an important operation in building a knowledge base. A user interface may facilitate data input by allowing the user to specify the experiment, its association with a particular study and/or project, and an experimental platform (e.g., an Affymetrix gene chip), and to identify key concepts with which to tag the data. In certain embodiments, data import also includes automated operations of tagging data, as well as mapping the imported data to data already in the system. Subsequent "preprocessing" (after the import) correlates the imported data (e.g., imported feature sets and/or feature groups) to other feature sets and feature groups.

Preprocessing—Preprocessing involves manipulating the feature sets to identify and store statistical relationships between pairs of feature sets in a knowledge base. Preprocessing may also involve identifying and storing statistical relationships between feature sets and feature groups in the knowledge base. In certain embodiments, preprocessing involves correlating a newly imported feature set against other feature sets and against feature groups in the knowledge base. The statistical relationships may be pre-computed and stored for all pairs of different feature sets having associated statistics and all combinations of feature sets having associated statistics and feature groups, although the invention is not limited to this level of complete correlation.

In one embodiment, the statistical correlations are made by using rank-based enrichment statistics. For example, a rank-based iterative algorithm that employs an exact test is used in certain embodiments, although other types of relationships may be employed, such as the magnitude of overlap between feature sets. Other correlation methods known in the art may also be used.

As an example, a new feature set input into the knowledge base is correlated with every other (or at least many) feature sets already in the knowledge base. The correlation compares the new feature set and the feature set under consideration on a feature-by-feature basis by comparing the rank or other information about matching genes. A rank-based iterative algorithm is used in one embodiment to correlate the feature sets. The result of correlating two feature sets is a "score." Scores are stored in the knowledge base and used in responding to queries.

Study/Project/Library—This is a hierarchy of data containers (like a directory) that may be employed in certain embodiments. A study may include one or more feature sets obtained in a focused set of experiments (e.g., experiments related to a particular cardiovascular target). A Project includes one or more Studies (e.g., the entire cardiovascular effort within a company). The library is a collection of all projects in a knowledge base. The end user has flexibility in defining the boundaries between the various levels of the hierarchy.

Tag—A tag associates descriptive information about a feature set with the feature set. This allows for the feature set to be identified as a result when a query specifies or implicates a particular tag. Often clinical parameters are used as tags. Examples of tag categories include tumor stage, patient age, sample phenotypic characteristics and tissue types. Tags may also be referred to as concepts.

Mapping—Mapping takes a feature (e.g., a gene) in a feature set and maps it to a globally unique mapping identifier in the knowledge base. For example, two sets of experimental data used to create two different feature sets may use different names for the same gene. Often the knowledge base includes an encompassing list of globally unique mapping identifiers in an index set. Mapping uses the knowledge base's globally unique mapping identifier for the feature to establish a connection between the different feature names or IDs. In certain embodiments, a feature may be mapped to a plurality of globally unique mapping identifiers. In an example, a gene may also be mapped to a globally unique mapping identifier for a particular genetic region. Mapping allows diverse types of information (i.e., different features, from different platforms, data types and organisms) to be associated with each other. There are many ways to map and some of these will be elaborated on below. One involves the search of synonyms of the globally unique names of the genes. Another involves a spatial overlap of the gene sequence. For example, the genomic or chromosomal coordinate of the feature in a feature set may overlap the coordinates of a mapped feature in an index set of the knowledge base. Another type of mapping involves indirect mapping of a gene in the feature set to the gene in the index set. For example, the gene in an experiment may overlap in coordinates with a regulatory sequence in the knowledge base. That regulatory sequence in turn regulates a particular gene. Therefore, by indirect mapping, the experimental sequence is indirectly mapped to that gene in the knowledge base. Yet another form of indirect mapping involves determining the proximity of a gene in the index set to an experimental gene under consideration in the feature set. For example, the experimental feature coordinates may be within 100 base pairs of a knowledge base gene and thereby be mapped to that gene.

Correlation—As an example, a new feature set input into the knowledge base is correlated with every other (or at least many) feature sets already in the knowledge base. The correlation compares the new feature set and the feature set under consideration on a feature-by-feature basis comparing the rank or other information about matching genes. A ranked based running algorithm is used in one embodiment (to correlate the feature sets). The result of correlating two feature sets is a "score." Scores are stored in the knowledge base and used in responding to queries about genes, clinical parameters, drug treatments, etc.

Correlation is also employed to correlate new feature sets against feature groups in the knowledge base. For example, a feature group representing "growth" genes may be correlated to a feature set representing a drug response, which in turn allows correlation between the drug effect and growth genes to be made.

2. Integrating Sequence-Centric Information into a Knowledge Base

Aspects of the present invention relate to integrating sequence-centric data into a knowledge base—a database of diverse types of biological, chemical and/or medical information. The following description presents one process by which knowledge base according to the present invention may be obtained. In one embodiment, the knowledge base contains feature sets and feature groups from a number of sources, including data from external sources, such as public databases, including the National Center for Biotechnology Information (NCBI). In addition, the knowledge base generally includes proprietary data obtained and processed by the database developer or user. A knowledge base may be updated by a developer or user as new public or private information from sequencing experiments becomes available.

FIG. 1 shows an overview of the process of integrating sequence-centric information into a knowledge base according to various embodiments. The process begins with receiving raw data from a particular sequencing or platform SNP or sequence region (SR) experiment or study (102). The raw data may be obtained from a public database, private sources, an individual experiment run in a lab, etc. In certain embodiments, the raw data is derived from genotyping platforms, gene expression profiling platforms, or other sequence-centric platforms. In certain embodiments, a researcher or clinician may use a platform to obtain genetic profile or other sequence information. In certain cases, the raw data as received is in condition to be imported into the knowledge base as a feature set. In other embodiments, once the raw data is received, it is curated to produce one or more sequence-centric feature sets (104). In certain embodiments, incoming data is in the form of sequence regions (e.g., as characterized by chromosome and coordinates, by named regions, etc.) and associated statistics and/or non-numerical information. In certain embodiments, incoming data is in the form of SNPs and associated statistics and/or non-numerical information. If present, associated statistical information might indicate the fold change or a p-value associated with each feature (e.g., sequence region), representing the change of the feature between the experimental and control conditions. Feature sets are generated from a particular study or experiment and are imported into the knowledge base (106).

Figure 2A:
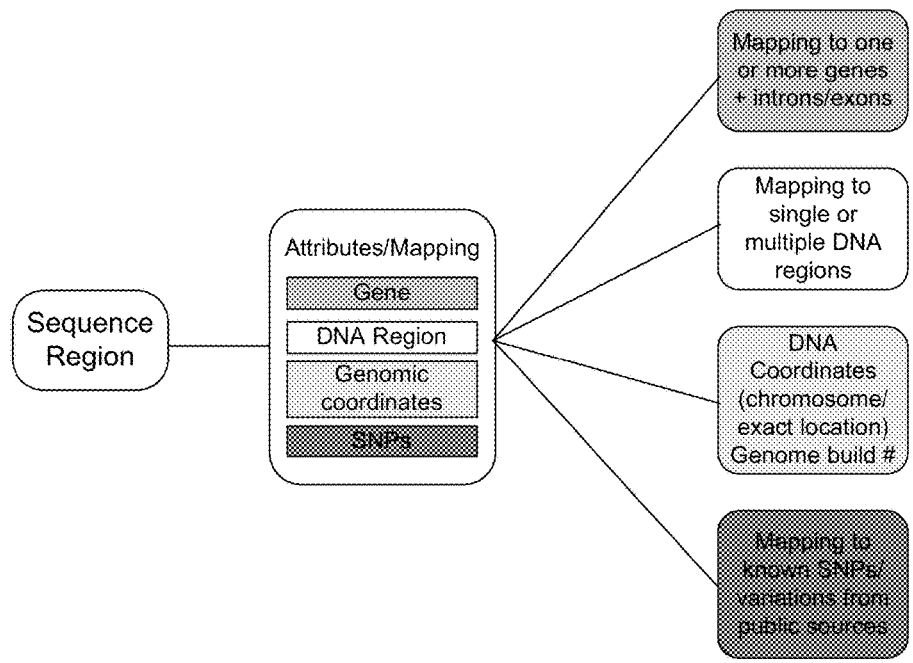
FIG. 2A presents an example of attributes/mappings for a sequence region according to various embodiments.
Figure 2B:
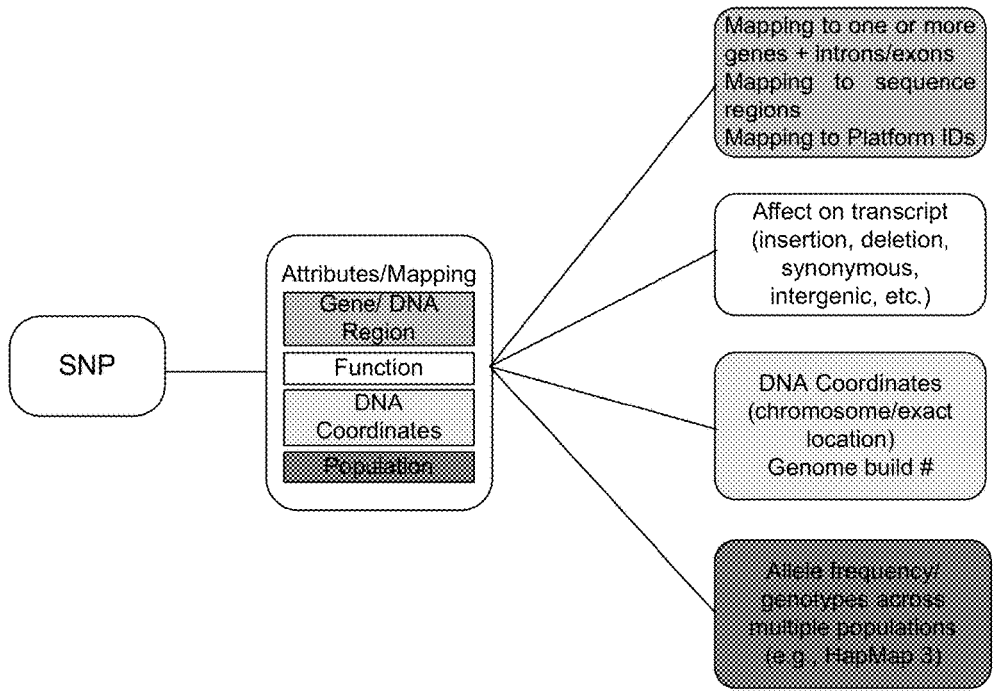
FIG. 2B presents a high level overview of an example of mappings and attributes for a single nucleotide polymorphism (SNP) according to various embodiments.

As described below, importing the data typically involves tagging the feature set with appropriate biomedical or chemical terms or concepts, as well as automatically mapping each feature in a feature set, i.e., establishing connections between each imported feature and other appropriate features in the knowledge base as appropriate. Various attributes such as organism, data type, population, etc. are associated with an imported feature (genomic region) on importing, including genomic coordinates, associated genes and transcripts (single or multiple genes overlapping or proximate and associated introns and exons), associated variations from public sources such as dbSNP (SNPs, CNVs, indels, deletions located within or close to a region of interest), experimentally derived genomic regions (newly discovered genomic regions from public studies and genomic regions from user's studies), and association type (different types of association, e.g., overlapping upstream, overlapping downstream, etc.) FIGS. 2A and 2B provide high-level overviews of attributes/mappings associated with sequences regions and SNPs according to various embodiments. First, in FIG. 2A, an example of attributes/mappings for a sequence region is shown. These include genomic coordinates as well as the following mappings: gene (mapping to one or more genes and introns/exons); DNA region (mappings to single or multiple DNA regions) and SNPs (mapping to known SNPs and/or variations from public sources or previously imported SNPs from experiments). In FIG. 2B, a high level overview of an example of mappings and attributes for a SNP is presented. Attributes include function (e.g., affect on a transcript); DNA coordinates, and population (e.g., allele frequency/genotypes across different populations). Mappings include mappings to genes, sequence regions and platform IDs. Further details of mapping processes are given below.

Returning to FIG. 1, the next major operation in producing a knowledge base is correlating the imported feature set with other information in the knowledge base (e.g., including other features sets, feature groups and/or concepts) for use in responding to queries (108). This includes correlating the sequence-centric information with gene-centric information in the knowledge base, as well as other sequence-centric information. In certain embodiments, correlating uses the previously obtained mapping information. Depending on the feature set and query type this operation may not be performed in certain instances of importing a feature set. After correlation scoring, the correlation, e.g., in the form of a p-value, of a feature set with other information in the knowledge base is stored. Once the process in FIG. 1 is performed, the user is able, by submitting queries and navigating, to efficiently explore and connect biological information contained in the knowledge base. The process illustrated in FIG. 1 may be performed anytime a user wishes to add experimental data to the knowledge base.

A. SNP-Centric and Sequence-Centric Data Types and Feature Sets

As indicated above, raw data may be obtained from various experimental methods and platforms including SNP identification and genotyping, comparative genome amplification analysis, gene and exon-level amplification analysis, methylation, PCR/bisulfite sequencing, ChIP (protein-DNA), microarray and sequence analysis, direct sequencing, etc. Curating is the process of generating feature sets to be imported from raw data. This may involve data quality control, normalizing data, removing outlying data and identifying valid clinical questions, genetic profiles, etc. (i.e., identifying possible feature sets). Specific examples of curating processes are described in U.S. patent application Ser. No. 11/641,539 (published as U.S. Patent Publication 20070162411), referenced above.

The sequence-centric feature sets include a list of sequence regions. Sequence regions may be identified by any appropriate identification, including name, marker or coordinates. The feature sets may also include statistics and/or non-numerical information associated with the features. Specific examples of sequence-centric feature sets that may be derived from experiments, research or public or private databases include SNP sequence data, SNP platform data, and sequence or platform Sequence Region (SR) data. SNP sequence data may be generated using sequencing technology, producing a set of SNPs, e.g., identified by chromosome and location, and associated information. SNP platform data includes individual SNP data (e.g., genotyping of a single individual measured on a genome-wide or targeted SNP platform) and aggregate SNP data. Aggregate SNP data may involve analysis of a large collection of individuals in a case-control type experiment, including data generated from genomic wide association studies (GWAS). While SNP data of an individual typically does not have statistics associated with the features, aggregate SNP feature sets may include summary statistics (e.g., p-value) associated with each marker, SNP or other feature. Sequence/platform Sequence Region (SR) data includes sequence regions and numerical and/or non-numerical information generated using sequencing technology or sequence region platforms. Platforms used to generate this data include ChIP (protein-DNA) sequencing, comparative genomic hybridization (CGH), chromosomal microarray analysis (CMA), RNA or miRNA sequencing and methylation.

Figure 3A:
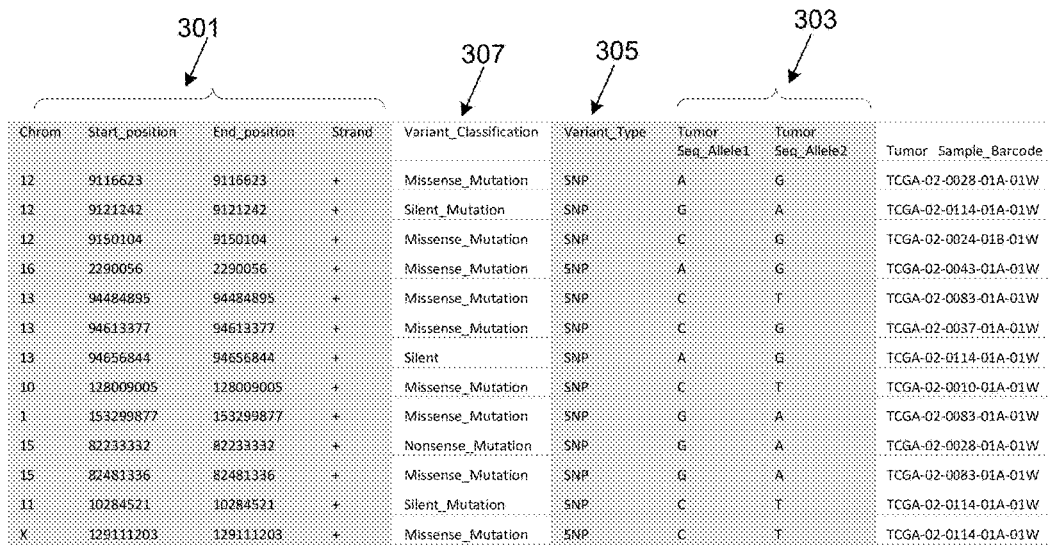
FIG. 3A presents an example of SNP genotyping obtained via sequencing for an individual.
Figure 3B:
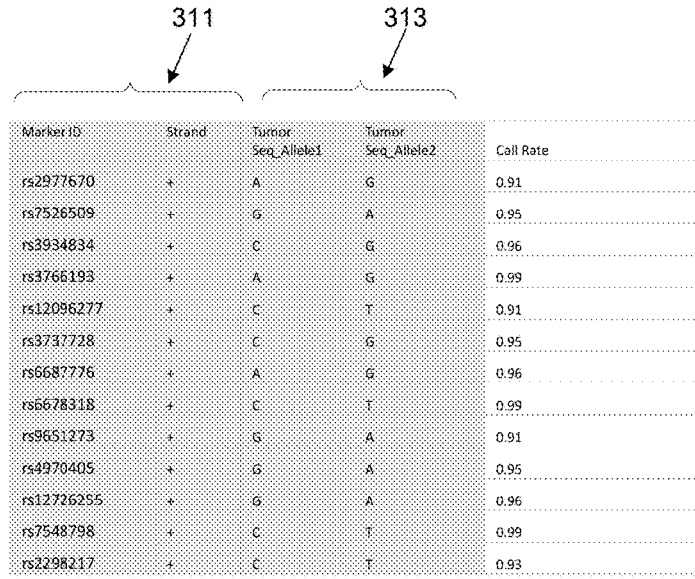
FIG. 3B presents an example of platform SNP data for an individual.

FIGS. 3A-3F shows sample sequence-centric feature set files to be imported into a knowledge base. FIGS. 3A and 3B show genotyping information for an individual. First, FIG. 3A shows SNP genotyping obtained via sequencing for an individual. Feature (SNP) identification information is indicated at 301. In this case, each SNP is identified by a chromosome, start and end positions (for SNPs, these are the same) and strand. Sequence information for each allele is shown at 303, with variant type shown at 305 and variant classification at 307. Other information may also be present in the data file. FIG. 3B is an example of platform SNP data for an individual. Feature identification information is indicated at 311, in this case reference SNP (rs) numbers and strand. Sequence information for each of two alleles is indicated at 313. Other information may be present, such as SNP call rate. FIG. 3C is an example of platform SNP aggregate data. This may include data from a genome wide association study (GWAS) and contain, for example, thousands of patients with and without diabetes, for each SNP what is the associated p-value and the major and minor allele. Information in the data file includes feature identification, here marker identification number, indicated at 321. Sequence information for each of two alleles is indicated at 323. Unlike the data files related to an individual shown in FIGS. 3A and 3B, the data file includes statistical information at 325, in this case p-values that provide an indication of genotypic association with a particular phenotype. In certain embodiments, this type of feature set is not correlated to gene expression or other feature sets, but is correlated to feature groups.

FIG. 3D shows another example of a SNP platform data file, in this case an arbitrary list of features (SNPs) as identified by identification numbers 331. The file also includes statistical information, in this case in the form of p-values 333 indicating a genotypic association. In certain embodiments, a sequence-centric feature set including a list of features related in some manner may or may not include associated statistical information. FIGS. 3E and 3F each show example sequence/platform sequence region (SR) data files. FIG. 3E shows a sample data file generated using DNA methylation. The data file contains features, in this example sequence regions (SRs) as indentified at 341 by chromosome and start and stop positions. Statistical information is also provided at 343. FIG. 3F shows a sample data file generating using ChIP-Seq (DNA-protein) methods. Sequence regions are identified as indicated at 351 by chromosome and start and stop positions. Statistical information is shown at 353. Other information may also be present. The above figures are just examples of the form sequence-centric feature sets may take as well as the sequence-centric data contained therein.

B. Importing

Figure 4:
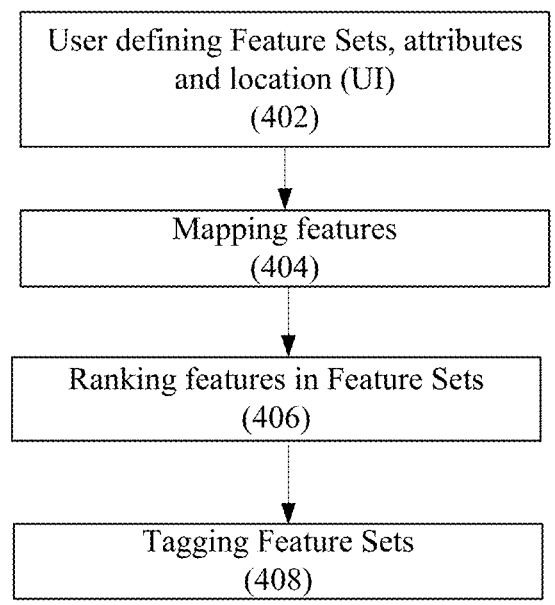
FIG. 4 is a process flow sheet that shows an overview of an importation process according to various embodiments.

Once the data is curated and organized in feature sets containing lists of features and associated statistics, if present, it is ready to be imported. The importation process involves importing the data into the system, tagging the data with standard terms that describe key concepts, and establishing connections between the imported data and other data within the system. FIG. 4 is a process flow sheet that shows an overview of the process.

The process begins in an operation 402, in which the user defines all relevant files (all feature set files) as well as other information needed for importation. The data import process is flexible enough to bring in diverse types of numeric and non-numeric fields associated with the sequence-centric feature sets. As described above, most incoming sequence-centric features sets include SNPs and associated statistics and/or non-numeric information and sequence regions and associated statistics and/or non-numeric information. Examples of information associated with each feature of various data types is given below:

SNP Sequence Data: Chromosome (e.g., 1, 2, 3, 4, etc.), Start/Stop Position (e.g., 14956, 14958, etc.), Strand (+/−), variation type (SNP, deletion, etc.), allele 1 sequence (e.g., G, T, C, A, TGGC, etc.) and allele 2 sequence (e.g., G, T, C, A, TGGC, etc.) Additional information may also be included such as variation classification (frameshift mutation, silent mutation, etc.).

SNP Platform Data (Individual): Marker ID (e.g., rs123456), Strand (+,−), allele 1 sequence (e.g., T), allele 2 sequence (e.g., G). Additional information may also be included.

SNP Platform Data (Aggregate): Marker ID (e.g., rs123456), Strand (+,−), summary statistics (e.g., p-value), risk allele sequence (e.g., A). Additional information may include minor allele (case) sequence, minor allele (control) sequence, etc.

Sequence Region (SR) Data: Chromosome, Start/Stop Position, Associated statistics. Additional information may include strand, region ID, etc.

For any feature sets to be imported, attributes to be recognized by the system, or if not recognized, assigned by the user include all or some of the following: organism (Human, Mouse, etc.), genome build number (35, 36, etc.), population (Caucasian, Asian, etc.), technology type (microarray, sequencing, QPCR, custom, etc.), experimental type (individual, aggregate (multiple samples) or other), and data type. As described above, in certain embodiments, data type may be categorized as follows: 1) SNP Sequence Data including individual SNP/Variation and aggregate SNP/Variation, 2) SNP Platform Data including individual SNP/Variation and aggregate SNP/Variation, and 3) Sequence Region Data including individual or aggregate data from sequencing technologies or sequence region platforms such as RNA-sequencing, miRNA sequencing, methylation, ChIP (protein-DNA) and CGH. Platform information (e.g., ABI, Illumina, Affymetrix, Sequenome, etc.) may also be included in certain embodiments.

In certain embodiments wherein the feature set to be imported contains associated statistics, a user may specify which column of statistics should be used for ranking the features within the feature set and correlating them. Associated information identified by a user may include text files that contain descriptions or lists of key concepts of the feature set. A location for the feature set in a directory system may also be specified. For example, the user may specify a Project directory and Study subdirectory.

The next operation in the data import process is sequence-centric mapping of the imported features (404). Mapping is the process through which diverse features (e.g., from different platforms, data types and organisms) are associated with each other. For example, a SNP may be associated with a sequence region of interest. During data importation, every feature is automatically mapped. In certain embodiments, mapping involves mapping each feature to one or more reference features or addresses in a globally unique mapping identifier set in the knowledge base (e.g., an Index Set). Mapping facilitates correlation between feature sets and between features sets and feature groups, allowing independent sets of data/information from diverse sources, assay types and platforms, to be correlated.

In certain embodiments, mapping involves the use of an Index Set that contains addresses or identifiers, each representing a unique feature (e.g., an Index Set may contain addresses or mapping identifiers representing a single gene of a human or non-human genome). Also in certain embodiments, mapping involves matching imported identifiers (e.g., generic name, etc.) to feature identifiers in the Index Set. These feature identifiers are various synonyms, genomic coordinates, etc., each of which points to one or more unique mapping identifiers. The mapping process may involve looking up feature identifier(s) that match an imported identifier, and then locating the mapping identifier(s) that the feature identifiers point to. In some cases, the best of a plurality of mapping identifiers is chosen for the mapping. Sequence-centric mapping of features based on their genomic coordinates is described further below.

Returning to FIG. 4, features are ranked in an operation 406. Ranking involves ordering features within each feature set based on their relative levels of response to the stimulus or treatment in the experiment(s), or based on their magnitude and direction of change between different phenotypes, as well as their ability to differentiate different phenotypic states (e.g., late tumor stage versus early tumor stage). Ranking is typically based on one or more of the associated statistics in an imported feature set; for example, features may be ranked in order of decreasing fold-change or increasing p-value. In certain embodiments, a user specifies what statistic is to be used to rank features. For certain feature sets that do not have associated statistics, ranking is not performed or may be performed based on imputed statistics.

Data tagging is performed in an operation 408 (operations 404-408 may be performed concurrently or in any order). Tags are standard terms that describe key concepts from biology, chemistry or medicine associated with a given study, feature set or feature group. Tagging allows users to transfer these associations and knowledge to the system along with the data. For example, if a study investigated beta blockers within a muscle tissue then the two tags may be "beta blockers" and "muscle." In addition, if a researcher knows that a given study is relevant to cardiovascular research, he/she can add a tag "cardiovascular disorders." Tagging may be performed automatically or manually. Automatic tagging automatically extracts key concepts for imported data. The system parses all text and documents associated with a given study and automatically captures and scores key concepts (e.g., based on frequency and specificity criteria) that match a database of tags—"standard" biomedical, chemical or other keywords. As indicated above, during the UI portion of the data import process, a user can specify additional files to be imported with the data, for example text descriptions of the experiments or studies. Automatic tagging parses these documents for terms that match tags in the database. In addition to automatic tagging, a user may "manually" or semi-automatically add tags to feature sets and feature groups. The user selects from tags in the database to associate with the feature sets and feature groups. In certain embodiments, the user may enter keywords to search the database. The search extracts the relevant tags and the user may add them to the imported data.

Figure 5A:
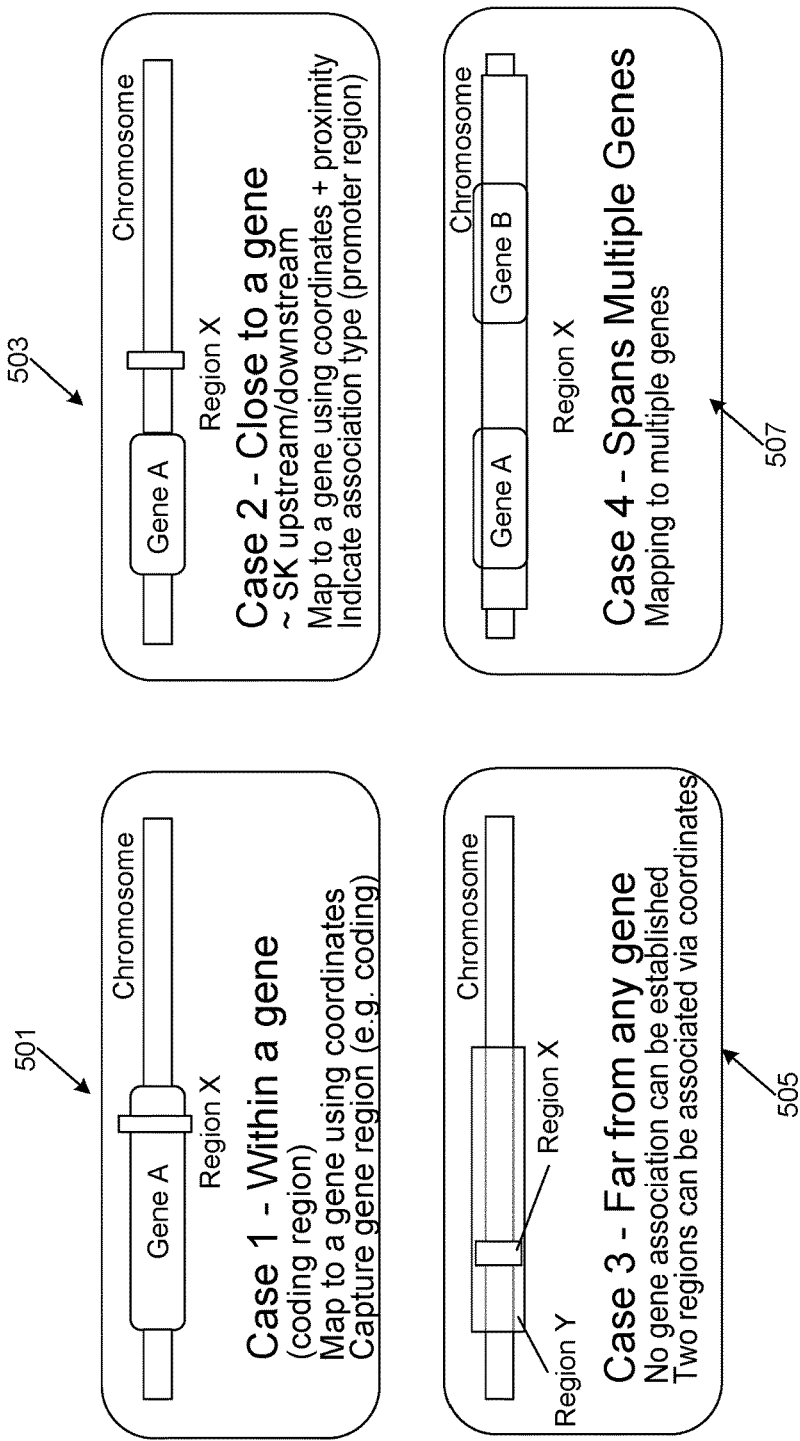
FIG. 5A presents examples of possible mappings of sequence region X according to various embodiments.

As discussed above, sequence-centric feature sets are mapped based on their genomic coordinates and genomic coordinates of genes and sequence regions within the knowledge base. Sequence-centric mapping creates associations between various features based on their genomic coordinates, e.g., using some prior research knowledge about relationships among different features or their physical proximity within the genome (in case of genes, SNPs or other sequence elements). For example, if a sequence region that is being imported falls within a given haplotype block, then associative mapping can be done between that sequence region and all genes within a given haplotype block. Another example is a sequence region that is located within a known binding site of a gene. The region is potentially related to that gene through the binding site that regulates it, and so can be mapped to it. Similarly features that overlap, are within, or are in close proximity to sequence regions that influence the activity of a gene may be mapped to the gene by sequence-centric mapping. FIG. 5A presents examples of possible mappings of sequence region X. First, at 501, the region X is mapped to gene A if it is within the coding region of gene A. At 503, the case in which the region is proximate to the gene (e.g., within 5 Kb) is depicted. In addition to being mapped to the gene, the type of mapping (e.g., promoter region) may be indicated and associated with the mapping. Even if sequence region is not proximate to any genes, it still may be mapped to features, such as other sequence regions. This is shown at 505, where region X is not associated with any gene, but is within region Y. The two regions are associated and a mapping is created via their genomic coordinates. Sequence-centric mapping is not necessarily 1:1, i.e., a given sequence can be mapped to multiple other features. An example of this is depicted at 507, wherein the region X spans and is mapped to multiple genes.

Exemplary implementations of sequence-centric mapping are described further below. According to various embodiments, mapping of features of sequence-centric features such as SNPs and sequence regions, takes place at multiple levels:

Mapping to know genes and intron/exon regions
Mapping to known variations (SNPs, CNVs)
Mapping to existing sequence regions in the knowledge base
Saving novel features to the knowledge base Mapping for sequence-centric regions is typically based on genomic coordinates of a standard genome build. If a feature set contains coordinates based on an older genome build, the original coordinates are typically converted to standard coordinates based on the standard genome build. According to various embodiments, mapping involves comparing the coordinates of genes, exons, SNPs and other sequence regions to define various mappings. These include:
S→G (sequence region to genes; sequence region to exons)
S→R (sequence region to genomic regions)
S2→S1 (sequence region to other sequence regions)
S→SNP (sequence region to SNP)
SNPimp→SNPref (SNP imported ID to reference SNP ID)
SNPref→G (reference SNP ID to genes, exons, introns)

Genomic regions R are known regions of certain biological activity, such as regions that are targeted by miRNAs. Genomic coordinates of genes (and their exons and introns), genomic regions R, SNPs, and sequence regions already in the knowledge base are used to facilitate mapping. Other mappings may be performed according to various embodiments, in addition to the ones listed above, including SNPref→R, SNPref→S1, etc. Other implementations of mapping based on genomic coordinates are within the scope of the invention.

Figure 5B:
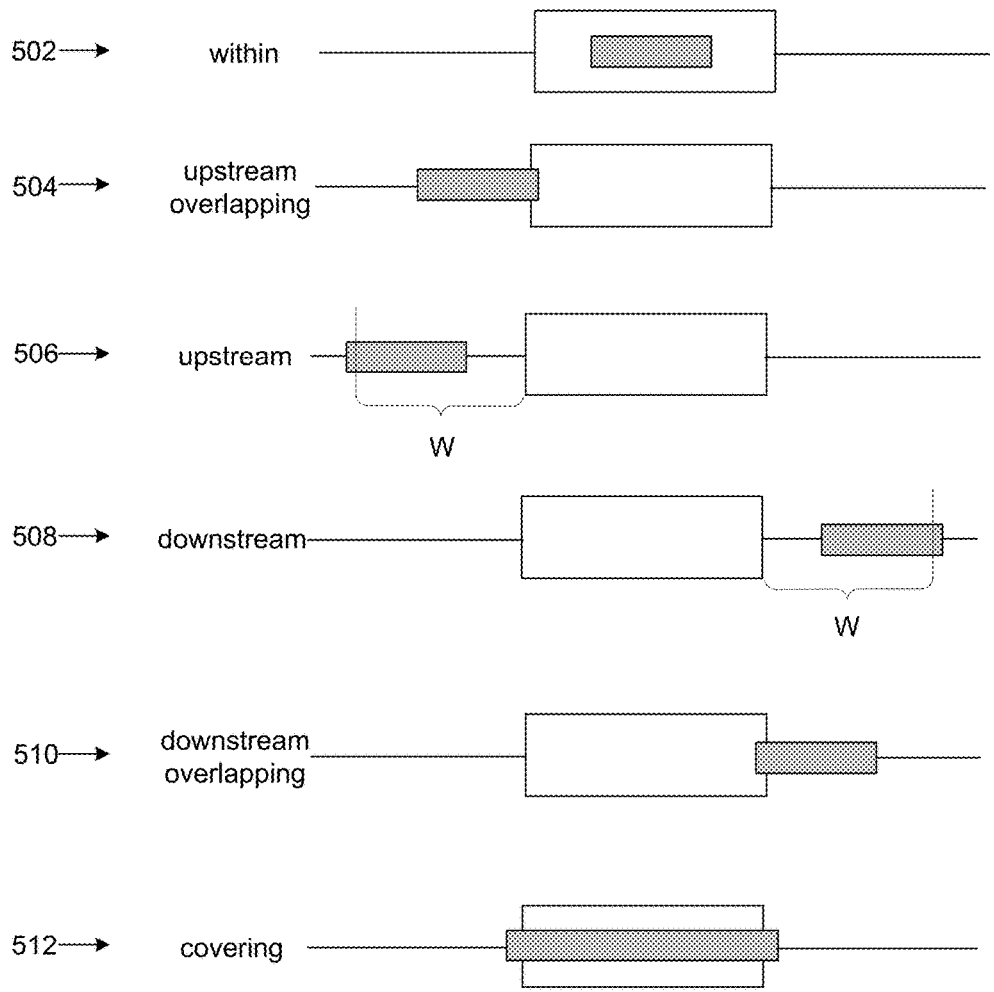
FIG. 5B illustrates mapping a sequence region S to a gene region G with different types of mappings according to various embodiments.

FIG. 5B illustrates mapping a sequence region S to a gene region G with different types of mappings, including S within G (502), S overlapping G upstream (504), S upstream of G within a certain proximity (defined by window W, e.g., 1-5000 base pairs) (506), S overlapping of G downstream of G (508), S downstream of G within a certain proximity (510) and S covering G (512). The window W may vary for 3' and 5' ends as well as for genes and sequence regions.

Note that typically multiple mappings are allowed, e.g., a given sequence region S can be mapped to multiple gene regions G. The mappings are stored along with the type of mapping in the knowledge base. (S1→G2, upstream overlapping; S1→G11, within; etc.). In this manner, features from sequence-centric feature sets are mapped to genes from gene-centric feature sets.

In certain embodiments, mapping to exons and introns of a gene is based on the type of mapping to the gene itself. In certain embodiments, where S→G is a downstream or upstream (no overlapping) mapping, S does not map to any exons or introns of G. Other types of mappings may be performed as shown in FIG. 5B (e.g., a sequence region S covering a gene G will map to all of the exons of G).

Mapping to a genomic region R or another sequence region S2 may be performed in the same manner as mapping to a gene region G as shown in FIG. 5B, with R or S2 replacing G. In certain embodiments, mapping SNPs includes mapping based on haplotype blocks. In this case, the knowledge based may contain haplotype blocks. For example, haplotype data, e.g., as presented in a haplotype map such as HapMap 2 or HapMap 3 may be used to build haplotype maps across a genome. In certain embodiments, linkage disequilibrium (LD) structures are used to build haplotype blocks and/or map a SNP to other SNPs from diverse feature sets based on function, phenotype, etc. $r^2$ correlation values between known SNPs in the knowledge base may be used to build haplotype blocks in certain embodiments. The haplotype blocks in the knowledge base are not limited to those defined by LD structures.

Figure 6:
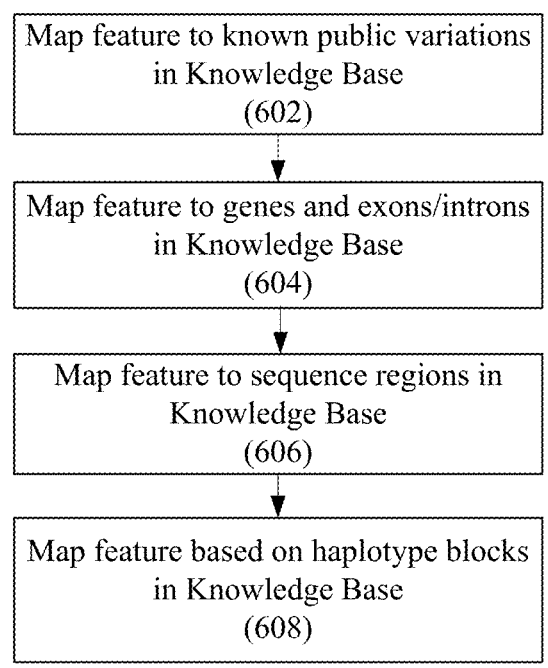
FIG. 6 is a process flow diagram showing operations in mapping features in feature set having SNP sequence data according to various embodiments.

FIG. 6 is a process flow diagram showing operations in mapping features in feature set having SNP sequence data. As indicated above, these feature sets typically contain a list of SNPs and/or variations as identified by chromosome and location. An example of a data file having SNP Sequence data is shown in FIG. 3A, above. First, the feature is mapped to known public variations (SNPs, del, CNVs, etc.) (602). This allows the system to distinguish known versus new variations, to link sequence regions to the results of genome-wide and target association studies, and to provide mechanistic explanations for associations between known SNPs and diverse phenotypes. The knowledge base may include known SNPs and variations, e.g., in a reference SNP table or other format, that contains SNP reference names, locations (chromosome and location), and strand information. Public sources of SNPs include dbSNP. In certain embodiments, mapping S→SNPref involves finding a reference SNP from a reference SNP table in the knowledge base that has the same location and chromosome as the imported SNP. Mapping is typically based on an exact match with the reference SNP. Strand information (in the form of +/− or top/bottom) may be stored during the import so that the orientation of the imported SNP relative to the reference SNP is readily derived. Next, the SNP is mapped to genes and exon/intron region (S→G) (604). This may be performed as described above with respect to FIG. 5B, with S being a single base pair. In certain embodiments, pre-computed mappings for each reference SNP stored in the knowledge base are used. Along with the mappings, the types of mappings (proximal region—upstream, downstream, overlapping—upstream, downstream, etc.) are stored. The SNP is then mapped to existing sequence regions in the knowledge base (S2→S1; S→R) (606). Again this performed as described above with respect to FIG. 5B. In certain embodiments, the SNP is mapped based on haplotype blocks (608). This may involve matching the imported feature to a reference SNP in a haplotype block, and mapping the imported feature to the haplotype block and/or features (SNPs, genes, etc.) within the block. Mapping is typically performed for all features in the feature set following this process.

Figure 7:
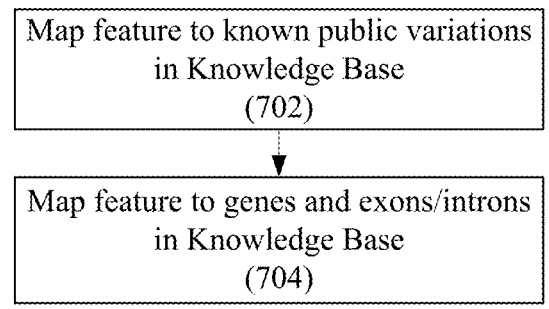
FIG. 7 is a process flow diagram showing operations in mapping features in feature set having SNP platform data according to various embodiments.

FIG. 7 is a process flow diagram showing operations in mapping features in feature set having SNP platform data. Features (SNPs) in such a feature set imported SNP may be identified by a platform ID. An example of a data file having SNP Platform data is shown in FIG. 3B, above. As with SNP sequence data, a feature is mapped to the feature is mapped to known public variations (SNPs, del, CNVs, etc.) (SNPimp 4 SNPref) (702). In the case of platform SNP data, the imported platform ID may be checked against platform IDs registered in the SNP reference table to establish the mapping SNPimp→SNPref. If the SNPimp does not match a platform identifier, it may be directly mapped to SNPref, while assigning a custom platform to the feature set. Once the imported SNP is mapped to a reference SNP, it is mapped to genes, exons and introns (SNPref→G) as described above with reference to FIG. 5B (704). Mapping type is stored as well. The system then checks whether there are more features to be mapped within the feature set under consideration. Mapping is performed for other features in the feature set. In certain embodiments, mapping to other sequence regions S1 or R in the knowledge base may also be performed. Further, haplotype or LD-based mapping may be performed as well for SNP platform data.

Figure 8:
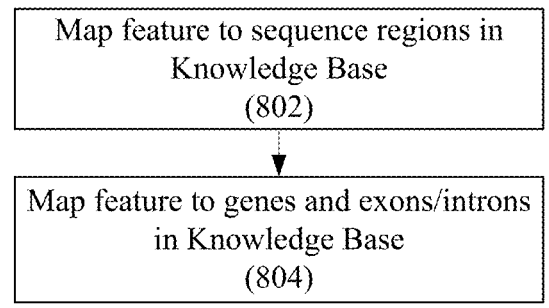
FIG. 8 is a process flow diagram showing operations in mapping features in a feature set having sequence region features according to various embodiments.

FIG. 8 is a process flow diagram showing operations in mapping features in a feature set having sequence region features. As indicated above, such features may be identified by location (chromosome and start/stop position). Mapping for the special case of a sequence region being a SNP (single base pair) is detailed above with respect to FIG. 6. First, the sequence region is mapped to existing sequence regions in the knowledge base (S2→S1; S→R) (802). The feature is then mapped to one or more genes, and exon and intron regions for each mapped gene (804). This is performed as described above with respect to FIG. 5B. Mapping is then typically performed for all features in the feature set.

In certain embodiments, mappings are weighted by the type of association between mapped features. For example, FIG. 5B above depicts six types of possible sequence-based mappings between a sequence region and a gene: within, upstream overlapping, upstream, downstream overlapping, downstream and covering. Each of these different association types may be given a different gene mapping weight (w1, w2, w3, etc.) reflecting the relative importance of the type of mapping to the correlation between the features. Similarly, mappings between sequence regions may also be given different region mapping weights (v1, v2, v3, etc.) depending on the association type.

After all features in a sequence-centric feature set have been mapped, each feature in the feature sets has a set of mapped genes, a set of mapped sequence regions, etc., with each mapping having a weight.

3. Pre-Computing Correlations Between Sequence-Centric Feature Sets and Other Information Once imported, sequence-centric feature sets are correlated with other information in the knowledge base, enabling researchers to interrogate genomic regions, variations, genes, pathways, and data sets across the entire information space, including gene-centric and sequence-centric data.

The sequence-centric mapping methods described in previous section enable associations between diverse types of data to be established. Once mapping is determined, correlation algorithms may be applied to pre-compute correlation scores (e.g., p-values and/or derivative rank scores) between a given set of data and any other information within the knowledge base.

According to various embodiments, correlations may be pre-computed and stored for use in responding to user queries, or may be computed on the fly as necessary to respond to queries. Three types of pre-computed correlations that may be performed for a particular sequence-centric feature set are: correlating sequence-centric feature sets with gene-centric feature sets; correlating sequence-centric features sets with feature groups; and correlating sequence-centric feature sets with other sequence-centric feature sets.

According to various embodiments, the correlations performed depend on the type of experimental data in a feature set. Correlations are made if it meaningful connections can be made between data sets. In an example, for feature sets containing genotyping/mutation data, correlations with feature groups are performed but correlations with other feature sets are not performed. For feature sets containing epigenetic profiling data, transcriptional data, and copy number variation, for example, feature sets may be correlated with other feature sets as well as feature groups.

According to various embodiments, correlation scoring is based on feature ranking within a feature set. Thus, prior to computing a correlation score, the features in a sequence-centric feature set are ranked by a statistic contained in the imported data file. For example, any of the following statistics may be used to assign ranks: descending order by abs(fold-change), i.e. the highest abs(fold-change) gets rank=1; descending order by score; ascending order by FDR, i.e. the smallest FDR gets rank=1, ascending order by p-value, etc. Thus, prior to computing a correlation score, the features in a feature set are ranked based on the p-value, fold change, or any other meaningful measurement or statistic contained in the feature table. The ranks may be normalized. It should be noted that not all sequence-centric feature sets contain statistical information; for example, a sequence-centric feature set may contain only genetic profile information for an individual. Accordingly, the features in these sequence-centric feature sets are not ranked. Pre-computed correlation scoring may not be performed for these feature sets according to various embodiments. In certain embodiments, p-values and/or correlated SNPs may be imputed for SNP feature sets. According to various embodiments, ranking sequence-centric feature sets may involve ranking sequence regions and/or genes. Ranking SNP-centric feature sets may involve ranking SNPs and/or mapped genes.

In certain embodiments, correlating a sequence-centric feature set with other information in the knowledge base uses the set of mapped genes for the sequence-centric feature set and their corresponding weighted mapped ranks and/or the set of mapped regions and their corresponding weighted mapped ranks.

In certain embodiments, the directional correlation scoring may be applied. Directional correlation scoring takes into account the direction of the correlation between feature sets, i.e., whether the correlation is positive or negative. A description of applying directional correlation between feature sets and a feature set and a feature group is given in U.S. patent application Ser. No. 12/234,435, published as U.S. Patent Publication 2009/0049019, incorporated by reference herein. The methods described therein may be applied to correlation scoring involving sequence-centric features sets. In certain embodiments, the methods involve correlation scoring using sub-feature sets containing a reduced number of features (e.g., all positively correlated features).

A. Sequence-Centric Feature Set to Gene-Centric Feature Set Scoring

In certain embodiments, correlating sequence-centric data with gene-centric data in performed by associating sequence regions with genes, e.g., as determined by mapping. These genes, borrowing the ranks of their respective regions, can then be compared to gene signatures, e.g., in the form of gene-centric feature sets, in the system. A rank-based enrichment algorithm may be used to calculate final enrichment p-values indicating the correlation between the sequence-centric data and the gene-centric data and the direction of the correlation. This correlation score and direction is then stored for later use in responding to user queries.

Figure 9:
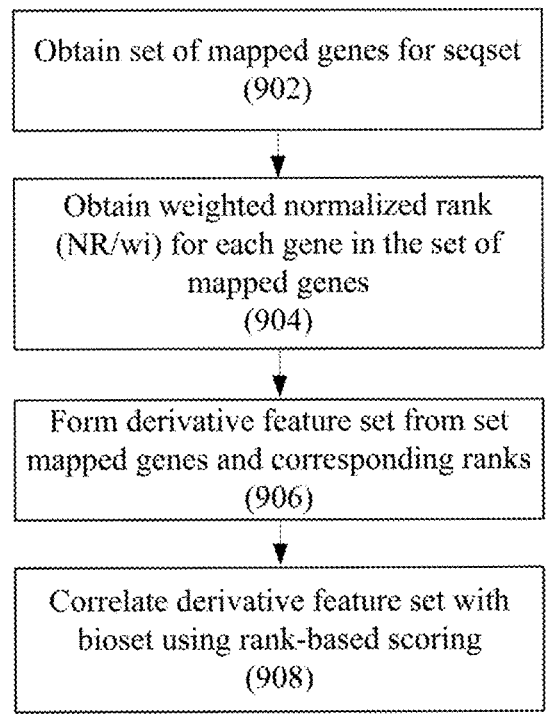
FIG. 9 shows a process flow diagram illustrating operations in a method of correlating a sequence-centric feature set (seqset) with a gene-centric feature set (bioset) according to various embodiments.

FIG. 9 shows a process flow diagram illustrating operations in a method of correlating a sequence-centric feature set (seqset) with a gene-centric feature set (bioset). First, the set of mapped genes for the seqset is determined (902). The weighted normalized rank for each gene in the set of mapped genes is then determined (904). The weighted normalized rank of a mapped gene may be given as the normalized rank of the sequence region feature to which the gene is mapped (NR) divided by the weight of the mapping: NR/wi. From the set of mapped genes and corresponding normalized weighted ranks, a derivative sequence-centric feature set having a bioset-like structure is then formed (906). Correlation scoring between the derivative sequence-centric feature set and the bioset is then performed (908).

Figure 10:
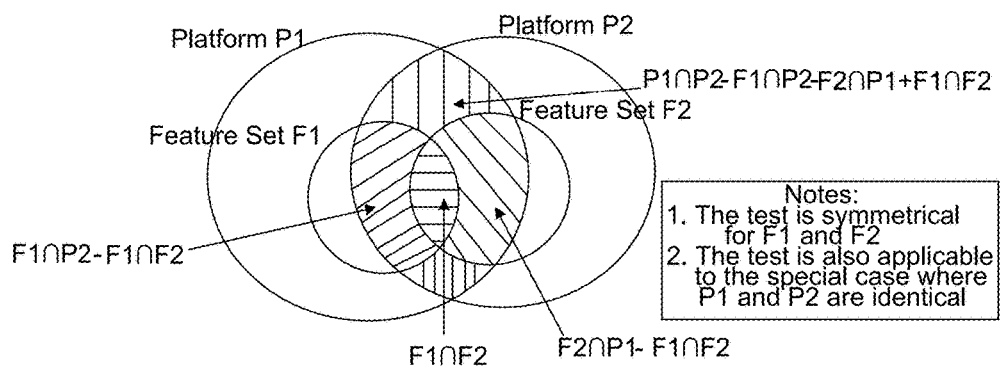
FIG. 10 is a feature set (F1) versus feature set (F2) set diagram, and table showing the elements or parameters to be used in Fisher's exact test measuring the significance of the overlap of the feature sets according to various embodiments.
Figure 11:
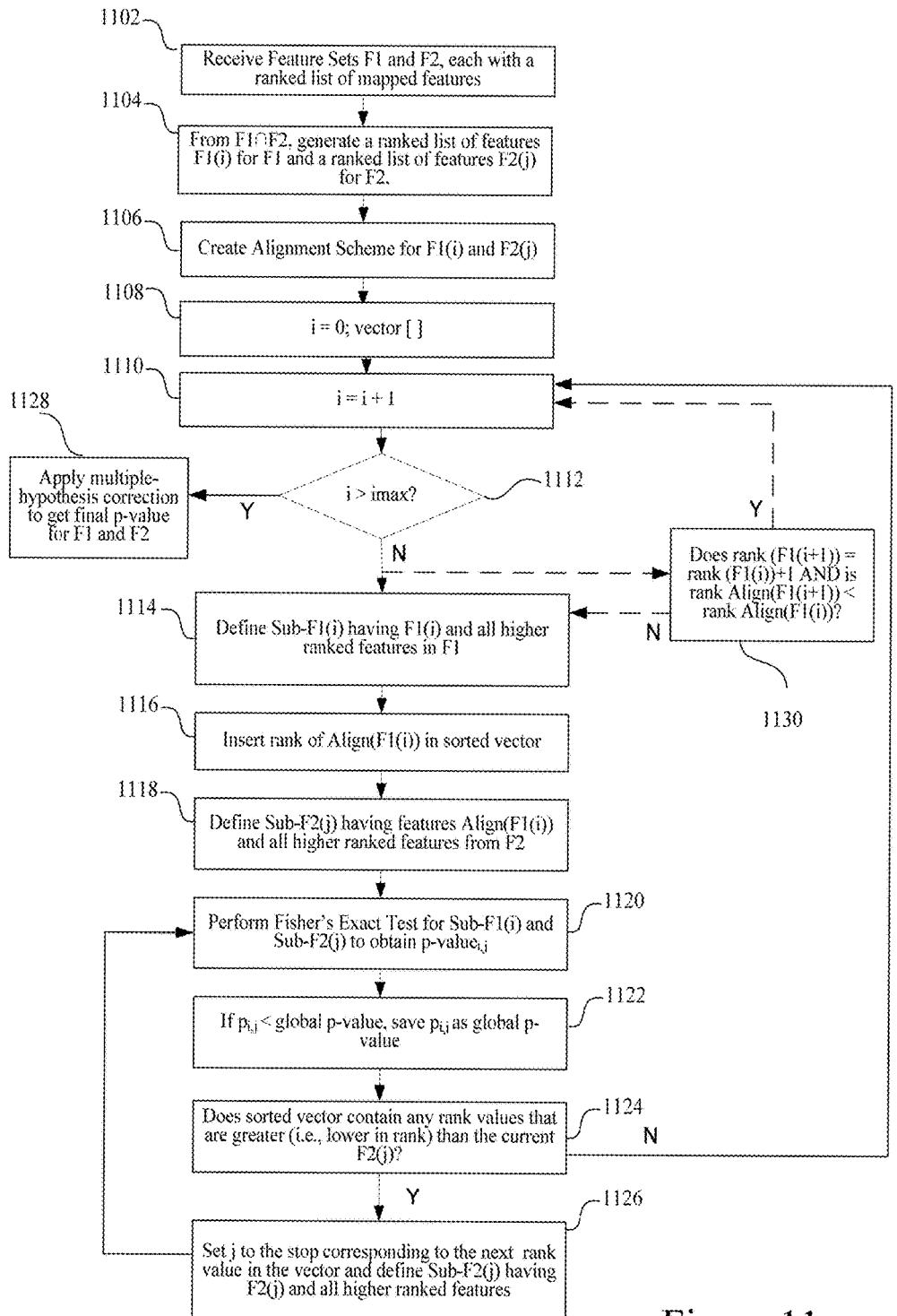
FIG. 11 is a process flow diagram showing key operations in generating a correlation score indicating the correlation between feature sets F1 and F2 according to various embodiments.

According to various embodiments, an iterative rank-based algorithm may be used to calculate a p-value or other score indicating the correlation between two feature sets such as a derivative feature set and a gene-centric bioset. The method takes into account two sets of rankings: those in the derivative feature set (i.e., the rankings of the mapped genes as determined in 904) and the rankings of the features in the gene-centric bioset. FIGS. 10 and 11 present examples of methods of employing an iterative rank-based algorithm to calculate a p-value indicating the correlation between two feature sets F1 and F2. FIG. 10 is a feature set (F1) versus feature set (F2) set diagram, and table showing the elements or parameters to be used in Fisher's exact test measuring the significance of the overlap of the feature sets. P represents all features in the experimental platform(s) (e.g., all features in the raw data); F1 represents the features in the feature set F1; and F2 represents the features in the feature set F2. The table below the set diagram shows the sets indicated on the diagram. The highlighted elements of the contingency table may be used in Fisher's exact test in accordance with embodiments of the invention. These elements are:

F1∩F2 is the intersect of feature set F1 and feature set F2, and is indicated in the diagram. This represents features in F1 that are mapped to features in F2;

F1∩P2−F1∩F2 represents the features in the intersect of P1 and P2 that are in F1, but are not in F2;

F2∩P1−F1∩F2 represents the features in the intersect of P1 and P2 that are in F2, but are not in F1;

P1∩P2−F1∩P2−F2∩P1+F1∩F2 represents the features in the intersect of P1 and P2 that are neither in F1 or F2.

Applying Fisher's exact test, a p-value is obtained. An implementation of Fisher's exact test based on Agresti A, (1992), A Survey of Exact Inference for Contingency Tables, *Statistical Science*, 7, 131-153, hereby incorporated by reference, may be used in certain embodiments.

FIG. 11 is a process flow diagram showing key operations in generating a correlation score indicating the correlation between feature sets F1 and F2. First, in an operation 1102, feature sets F1 and F2 are received, each with a ranked list of mapped features. The intersect F1∩F2 is determined using the mapping identifiers. From F1∩F2, a ranked list of features F1(i) and F2(j) are generated in an operation 1104. The variables "i" and "j" are used to designate stops or checkpoints of F1 and F2, respectively. Stops are used to define sub-feature sets for which to generate p-values, the lowest of which is the final p-value for the feature set to feature set comparison. In a brute force method, Fisher's exact test would be performed for all combinations of sub-F1(i) Sets and all possible sub-F2(j) sets. However, this is not necessary, as reflected in the algorithm below. All i=1 to i=imax stops in F1(i) are indexed over in an outer loop. The inner loop, however, does not index over all possible values of j, but determines what sub-F2 Sets to use based on a sorted vector. In this sense, "j" indicates the current stop of F2 being used to define the sub-F2 Set, from which a p-value $p_{i,j}$ is calculated. Note that though the features in F1(i) and F2(j) are the same (i.e., all overlapping features from F1 and F2), the ranked lists are different as the F1 and F2 have different rankings.

F1(i) and F2(j) are then 'aligned,' i.e., each feature F1(i) is connected to or associated with its corresponding feature F2(j) (1106). For example, F1(1) may be aligned with F2(3); F1(2) aligned with F2(2); F1(3) aligned with F2(4), etc. The nomenclature Align(F1(i)) is used in the flow sheet and in the following description to refer to the feature in F2(j) that F1(i) is aligned to; for example, Align(F1(3)) refers to F2(4). Similarly Align(F2(3)) refers to F1(1). A counter i is set to zero (1108). Operation 1108 also indicates that a sorted vector used later in the algorithm to determine sub-F2 Sets is empty at this point. Counter i is indexed (i=i+1) at an operation 1110. Counter i is compared to imax, where imax is the number of features in F1(i) (1112). If it is less than or equal to imax, the process proceeds to an operation 1114, in which a sub-feature set sub-F1(i) is defined. (Operation 1130 is an optimization step that is discussed further below). Sub-F1(i) contains F1(i) and all higher ranked features in F1. The rank of Align(F1(i)) is then inserted into the vector (1116). For F1(1), the vector would be [13]; for F1(2), the vector would be [2,13], etc. The process then defines a sub-feature set sub-F2(j) in an operation 1118. Sub-F2(j) contains Align(F1(i)) and all higher ranked features in F2. For i=1, Align(F1(1))=F2(3). The rank of F2(3) is 13, so sub-F2(j) contains the features in F2 ranked 1-13. Fisher's exact test is then performed for sub-F1(i) and sub-F2(j) using the parameters described above with respect to FIG. 10 to generate a p-value $p_{i,j}$ (1120). The p-value $p_{i,j}$ is then compared to the global p-value and saved as the global p-value if it is lower (1122). Determining if the current sub-F1(i) should be compared to other sub-F2 sets involves checking if the sorted vector contains any rank values that are higher (i.e., lower in rank) than the rank of the current F2(j) (1124). If it does, j is set to the stop corresponding to the next rank value in the vector and a new sub-F2(j) containing F2(j) and all higher-ranked features in F2 is defined (1126). For example, for the first iteration of the inner loop for i=2 in the example shown in FIG. 11C, j=1 (Align(F1(2))=F2(1)). The rank of F2(1) is 2, so the vector contains [2,13]. First a p-value $p_{2,1}$ is calculated. Then the vector is checked to see if contains any ranked values that are greater (lower in rank) than the rank of 2. It does as 13 is greater than 2 (also stated as 13 is lower in rank than 2). A new sub-F2(j) is created using the F2 stop corresponding to rank 13 as the new j; in this case sub-F2(3) is created, containing the F2 features ranked 1-13. The process then returns to operation 1120, in which Fisher's exact test is performed for F1(i) and the new F2(j). Returning to operation 1124, if there are no rank values greater than the rank of current F2(j), the process returns to operation 1110 to calculate p-values for the next F1 stop. Once all F1 stops have been run through and i>imax, a multiple hypothesis testing correction is applied (1128). This correction is based on the total number of possible hypothesis tests, i.e., all possible combinations of F1 and F2 sub-feature sets and accounts for the fact that larger feature sets return lower p-values, as there are more opportunities for lower p-values to be received with larger feature sets. Multiple-hypothesis testing corrections are known in the art. This final p-value is then stored, e.g., in a Scoring Table. In certain embodiments, a 'rank score' is stored in the Scoring Table in addition to or instead of the final p-value. Briefly, the rank score is a derivative of the final p-value and is the negative logarithm of the p-value.

Further details of this example of generating a p-value indicating a correlation between F1 and F2, including optimizations, are given in above-referenced U.S. patent application Ser. No. 11/641,539 (published as U.S. Patent Publication 20070162411) and U.S. patent application Ser. No. 12/234,435 (published as U.S. Patent Publication 2009/0049019), both of which are incorporated by reference herein, including various optimizations that may be implemented to improve computational efficiency.

B. Sequence-Centric Feature Set to Sequence-Centric Feature Set Scoring

Feature sets containing ranked sequence regions may be correlated by determining the overall amount of overlapping nucleotides from the combined set of regions and using it as a basis for determining correlations. The entire genome sequence may be used as the background.

Figure 12:
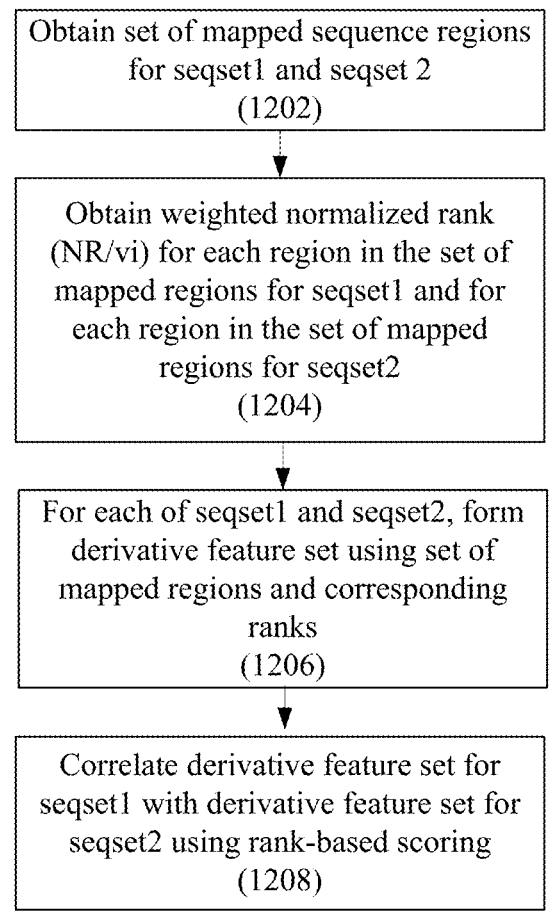
FIG. 12 shows a process flow diagram illustrating operations in a method of correlating two sequence-centric feature sets (seqset 1 and seqset 2) according to various embodiments.

FIG. 12 shows a process flow diagram illustrating operations in a method of correlating two sequence-centric feature sets (seqset 1 and seqset 2). First, the set of mapped regions for each seqset is determined (1202). This set includes all sequence regions, genomic regions, etc. that the features in a seqset are mapped to as described above with respect to FIG. 5B. The weighted normalized rank for each sequence region in the set of mapped sequence region is then determined (1204). The weighted normalized rank of a mapped sequence region may be given as the normalized rank of the sequence region feature to which the sequence region is mapped (NR) divided by the weight of the mapping: NR/vi.

From the set of mapped sequence regions and corresponding normalized weighted ranks, derivative sequence-centric feature sets are then formed, each derivative feature set having a list of ranked sequence region features (1206). Correlation scoring between the derivative sequence-centric feature sets is then performed (1208). An iterative rank-based algorithm may be used as described above for sequence-centric feature set to gene-centric feature set scoring.

C. Sequence-Centric Feature Set to Feature Group Scoring

Figure 13:
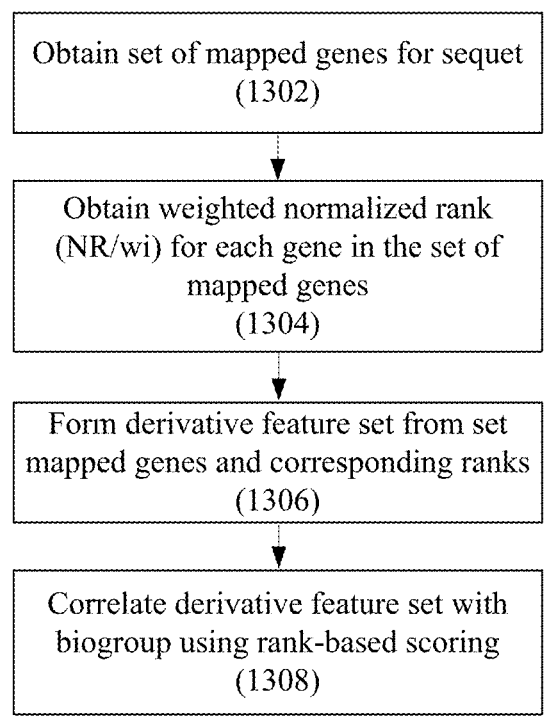
FIG. 13 shows a process flow diagram illustrating operations in a method of correlating a sequence-centric feature set (seqset) and a feature group (biogroup) according to various embodiments.

FIG. 13 shows a process flow diagram illustrating operations in a method of correlating a sequence-centric feature set (seqset) and a feature group (biogroup). As with the sequence-centric feature set to gene-centric feature set scoring, the set of mapped genes for the seqset is determined (1302). The weighted normalized rank, equal to NR/wi, for each gene in the set of mapped genes is then determined (1304). From the set of mapped genes and corresponding normalized weighted ranks, a derivative sequence-centric feature set having a bioset-like structure is then formed (1306). Correlation scoring between the derivative sequence-centric feature set and the feature group is then performed (1308).

Figure 14:
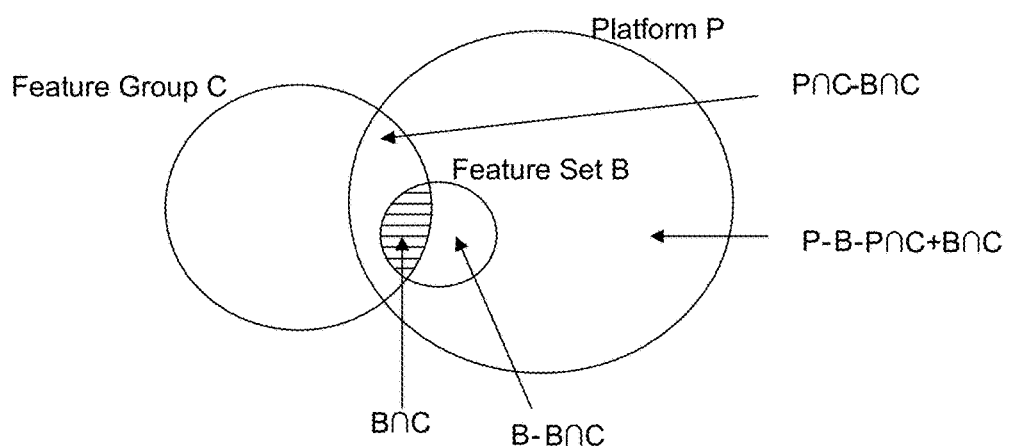
FIG. 14 is a feature set versus feature group set diagram illustrating elements used in a rank-based algorithm to determine the correlation between a feature set and a feature group according to various embodiments.

Correlation scoring between a feature set and a feature group is described in as U.S. Patent Publication 20070162411) and U.S. patent application Ser. No. 12/234,435 (published as U.S. Patent Publication 2009/0049019), both of which are incorporated by reference herein. Briefly, the method is analogous to the feature set to feature set scoring described above, though simpler as only one set of ranks need to be considered. FIG. 14 is a feature set versus feature group set diagram illustrating elements used in a rank-based algorithm to determine the correlation between a feature set and a feature group. P represents all features in the experimental platform (e.g., all genes that a microarray test measures expression of or all features in the raw data); B represents the features in the feature set; and C represents the features in the feature group. The table below the set diagram shows the sets indicated on the diagram. The elements of the contingency table used in Fisher's exact test in accordance with embodiments of the invention are highlighted in the table in FIG. 14. These elements are:

B∩C is the intersect of feature set B and feature group C, and is shown as the striped subset in the diagram. This represents features in B that are mapped to features in C.

P∩B−B∩C represents the features in P that are mapped to C, but are not in B, and is indicated on the diagram;

B−B∩C represents the features in B that are not mapped to features in C and is indicated on the diagram;

P−B−P∩C+B∩C represents the features in P that are neither in B nor mapped to features in C. This subset is also indicated on the diagram.

Ranked sequence-centric data sets may be correlated to other ranked feature sets and feature groups after importation. These correlations may be then stored in a scoring table for use in responding to user queries. In certain embodiments, it correlating sequence-centric feature sets to feature groups or other information in the knowledge base may use the set of mapped regions and corresponding ranks.

D. Concept Scoring

In certain embodiments, pre-computations also include concept scoring to determine the relevance or correlation of various biological concepts with the other information in the database, such as features, feature sets and feature groups. As described above, in certain embodiments, the knowledge base contains an ontology or taxonomy, i.e., a hierarchical structure of concepts as identified by tag or scientific term. An example of such a structure is Diseases/Classes of Diseases/Specific Diseases in each Class. The knowledge base may also contain a list of all feature sets and feature groups associated with each tag. The tags and the categories and sub-categories in the hierarchical structure are arranged in what may be referred to as concepts. Each node of the structure represents a medical, chemical or biological concept. In this manner, scientific concepts are categorized. For example, a categorization of stage 2 breast cancer may be: Diseases/Proliferative Diseases/Cancer/Breast Cancer/Stage 2 Breast Cancer, with disease the top-level category. Each of these—diseases, proliferative diseases, cancer, breast cancer and stage 2 breast cancer—is a medical concept that may be used to tag other information in the database. The taxonomy may be a publicly available taxonomy, such as the Medical Subject Headings (MeSH) taxonomy, Snomed, FMA (Foundation Model of Anatomy), PubChem Features, privately built taxonomies, or some combination of these. Examples of top-level categories include disease, tissues/organs, treatments, gene alterations, and feature groups.

Categorization and concept scoring is described in detail in U.S. patent application Ser. No. 12/398,107, filed Mar. 4, 2009, incorporated by reference herein. In certain embodiments, concept scoring is performed to score concepts with each of features, feature sets and feature groups. The concept scores are stored, e.g., in a concept scoring table to be used to respond to user queries.

Figure 15:
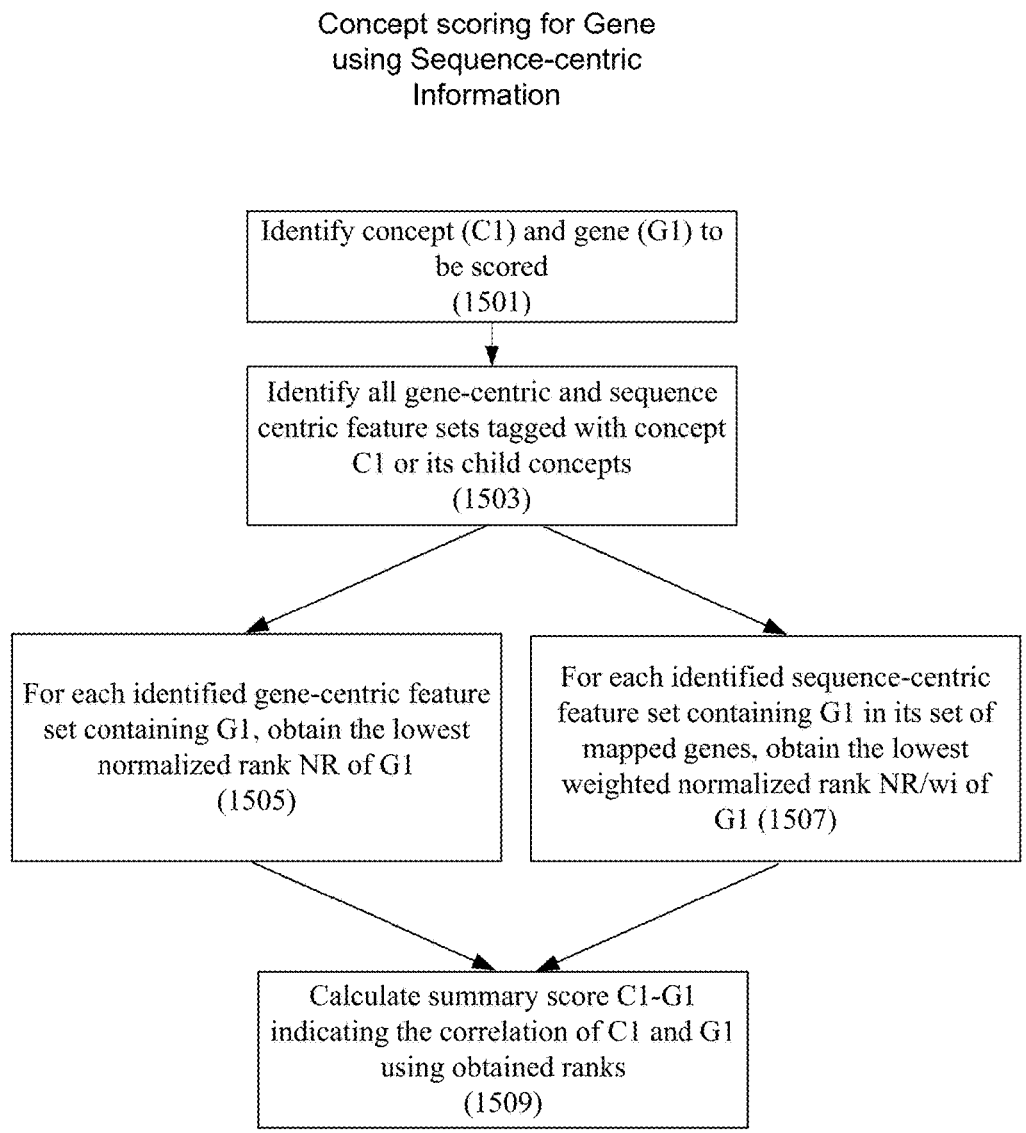
FIG. 15 is shows a process flow diagram illustrating operations in scoring concept C1 (e.g., breast cancer) with gene G1 (e.g., bcra1) according to various embodiments.

In certain embodiments, each sequence-centric feature set contributes to a concept score via its set of mapped genes and the corresponding weighted ranks described above. An example is given in FIG. 15, which is a flow diagram illustrating operations in scoring concept C1 (e.g., breast cancer) with gene G1 (e.g., bcra1). As depicted, the process begins by the system identifying a concept C1 and a feature G1 to be scored (1501). In many embodiments, the process determines a score for each possible pair of concept and feature, and so iterates over all possible combinations. In other embodiments, there may only be a subset of features and/or taxonomy concepts for which a concept score is calculated. After setting the concept and feature for the current iteration, the process next identifies all feature sets that are tagged with 1) the current concept or 2) its children concepts (1503). For example, a feature set tagged only with the concept "stage 2 breast cancer," would be identified for the concept 'stage 2 breast cancer' as well for its' parent concept, "breast cancer."

Although not depicted, the identified feature sets may be filtered to remove (or in certain embodiments, reweight) feature sets that are less relevant to the concept or that would skew the results. The process then identifies contributions to the concept score of each of the remaining feature sets: for a gene-centric feature set via its feature rankings and for a sequence-centric feature set via the set of its mapped genes and the corresponding weighted ranks. So, for all identified (and filtered, if applicable) gene-centric feature sets, the lowest normalized rank of G1 for each feature set containing G1 is obtained (1505). For all such sequence-centric feature sets, the lowest weighted normalized rank of G1 for each feature set containing G1 in its set of mapped genes is obtained (1507). A summary score or other overall score an overall score C1-G1 indicating the relevance of the concept to the feature is calculated using the lowest ranks determined in 1505 and 1507 is then calculated. (1509). Various other attributes may be used in addition to the ranks determined in 1505 and 1507, including the number of feature sets tagged with the concept, etc. Other methods of identifying the contribution of a sequence-centric feature set via its set of mapped genes and/or the contribution of a gene-centric feature set via its features may also be used.

Figure 16:
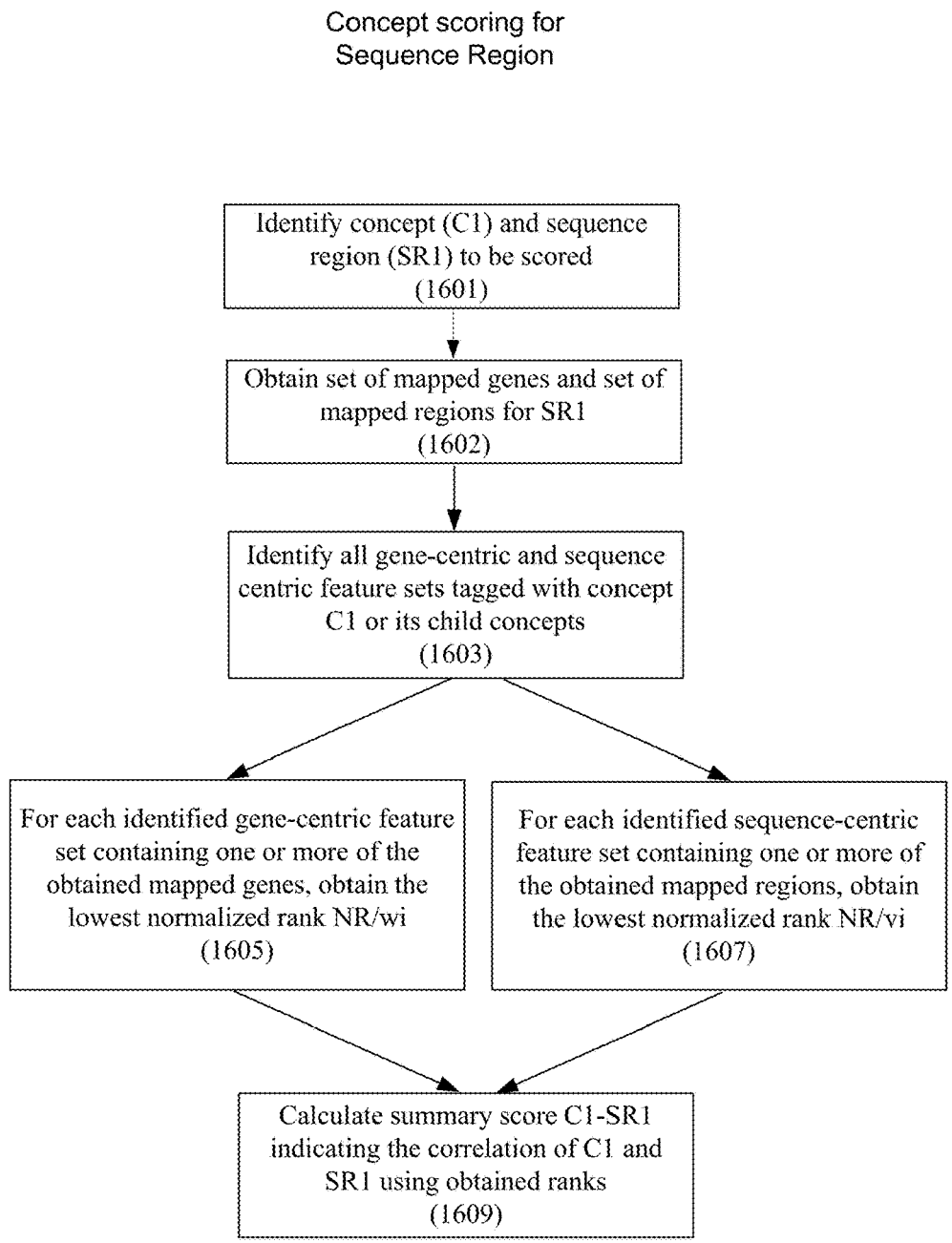
FIG. 16 shows a process flow diagram illustrating operations of obtaining a concept-sequence region score (C1-SR1) for a sequence region SR1 according to various embodiments.

Concept scoring may also be applied to a sequence region using the set of mapped genes and set of mapped regions for the sequence region in question. An example of obtaining a concept-sequence region score (C1-SR1) for a sequence region SR1 is described in FIG. 16. As depicted, the process begins by the system identifying a concept C1 and a sequence region SR1 to be scored (1601). In many embodiments, the process determines a score for each possible pair of concept and sequence region, and so iterates over all possible combinations. In other embodiments, there may only be a subset of sequence regions and/or taxonomy concepts for which a concept score is calculated. The process then obtains the set of mapped genes and set of mapped regions for the sequence region SR1 (1602). After setting the concept and feature for the current iteration, the process next identifies all feature sets that are tagged with 1) the current concept or 2) its children concepts (1603). As indicated above, these identified feature sets may be filtered at this point. The process then identifies contributions to the concept score of each of the remaining feature sets based on the set of mapped regions and the set of mapped genes obtained in 1602: for a gene-centric feature set via the mapped genes and the corresponding weighted ranks and for a sequence-centric feature set via the set of its mapped regions and the corresponding weighted ranks. So, for all identified (and filtered, if applicable) gene-centric feature sets, the lowest normalized weighted rank (NR/wi) of each gene-centric feature set containing one or more mapped genes is obtained from the weighted ranks of the mapped genes in the feature set (1605). For all such sequence-centric feature sets, the lowest weighted normalized rank (NR/vi) for each feature set containing on or mapped regions is obtained (1607). A summary score or other overall score an overall score C1-G1 indicating the relevance of the concept to the feature is calculated using the lowest ranks determined in 1605 and 1607 is then calculated. (1609). Various other attributes may be used in addition to the ranks determined in 1605 and 1607, including the number of feature sets tagged with the concept, etc.

Concept scoring for gene-centric and sequence-centric feature sets may also be performed as described in U.S. patent application Ser. No. 12/398,107, with sequence-centric feature sets taken into account. This may be done in certain embodiments using the feature set correlation scoring described above. Similarly concept scoring for feature groups may be performed as described in U.S. patent application Ser. No. 12/398,107 with sequence-centric feature sets taken into account via the sequence-centric feature set—feature group scoring described above.

In certain embodiments, concept scores may be stored for each feature, feature set and feature group scored. A list of contributing feature sets to the score as ordered by rank information may also be stored for use in responding to queries.

In certain embodiments, concept scores for a particular concept may be obtained using data sets different individuals (e.g., sequence SNP feature sets from different individuals) that are tagged with that concept. For example, concept scores for certain variations, SNPs, or genomic regions associated with the concept may be obtained using these feature sets.

4. Queries

The above description of methods, computational systems, and user interfaces for creating and defining a knowledge base provides a frame work for describing a querying methodology that may be employed with the present invention. The querying methodology described herein is not however limited to the specific architecture or content of the knowledge base presented above. Generally, a query involves (i) designating specific content that is to be compared and/or analyzed against (ii) other content in a "field of search" to generate (iii) a query result in which content from the field of search is selected and/or ranked based upon the comparison. As examples, a user may query a feature, e.g., a gene or a registered sequence region, a user-defined sequence region, a feature set, a feature group or a concept. A query may be limited to a particular field of search within the knowledge base. The search may include the entire knowledge base and this may be the default case. The user may define a field of search or the system may define it automatically.

Examples of queries include genes vs. feature sets (gene-centric feature sets and sequence-centric feature sets, including SNP-centric feature sets); sequence region vs. feature sets; sequence-centric feature set vs. genes; and SNP vs. SNP feature sets. These are examples of queries that may be executed in real-time. Feature set vs. feature set and feature set vs. feature group queries typically rely on pre-computations of correlation scores. Concept queries may also rely on pre-computations of concept scores.

As indicated, one type of query is a feature query. The query input to feature query is an individual feature (e.g., a gene, SNP, chemical compound, etc.). In certain embodiments, running the feature query involves identifying feature sets containing the feature of interest within a knowledge base. The identified feature sets may be ranked based upon the ranking of the feature within the feature sets.

Figure 17:
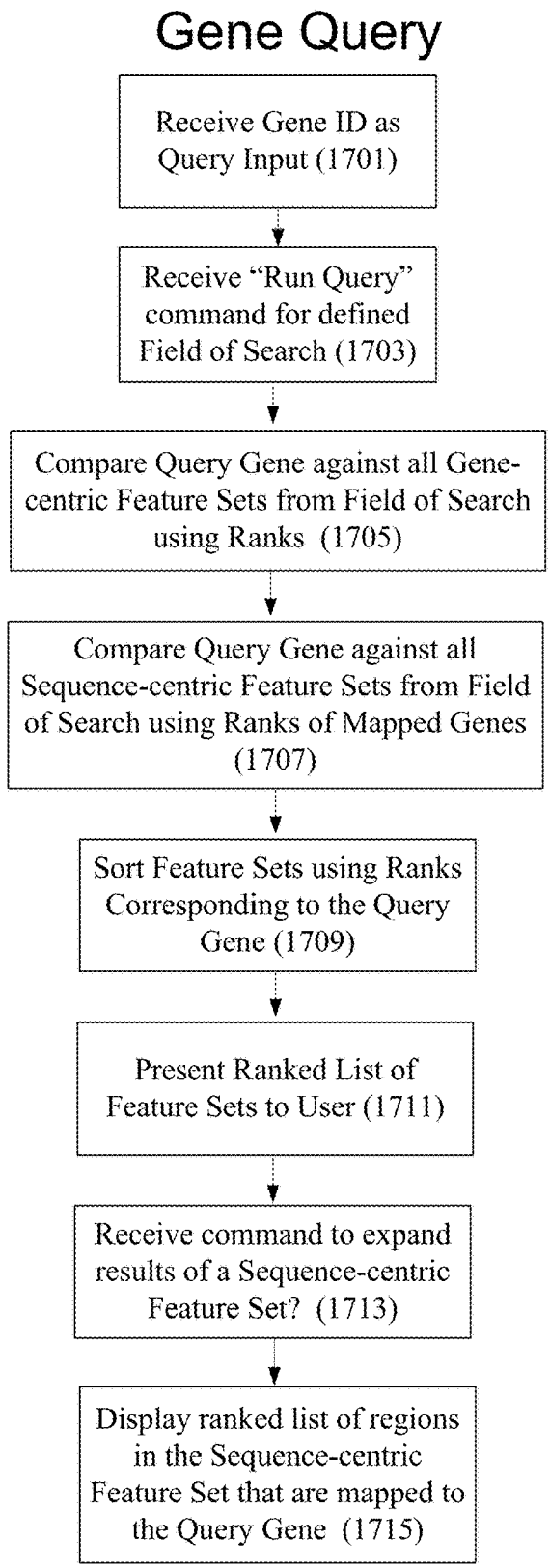
FIG. 17 is a flow diagram depicting operations in a methodology of querying a gene according to various embodiments.

In certain embodiments, the field of search of a feature query includes sequence-centric feature sets as well as other feature sets, e.g., gene-centric feature sets. FIG. 17 is a flow diagram depicting operations in a methodology of querying a gene according to certain embodiments. As illustrated, the process begins by receiving the identity of a gene (1701) followed by receiving a "Run Query" command (1703). In certain embodiments, the gene as queried is translated into a feature ID used within the system to identify the gene. The query is run by comparing the query gene against all gene-centric feature sets in the field search (1705). The comparison identifies those feature sets possessing the query feature, as well as the smallest normalized rank of the gene within each of these feature sets. Next, the query gene is compared against all sequence-centric features in the field of search (1707). The comparison identifies all the sequence-centric features sets possessing the query gene in their respective sets of mapped genes, as well as the lowest normalized weighted rank of the gene (NR/wi) for each of the identified sequence-centric feature sets. Next the system sorts the identified feature sets by the normalized ranks or normalized weighted ranks of the query feature within each of the identified feature sets (1709). For example, in one feature set, the gene may have a ranking of 6 and in another feature set, the same feature may have a weighted rank of 4.5. The latter feature set would be given a higher rank. The next operation in the depicted feature query involves presenting to the user the ranked list of Feature Sets (i.e., the query result) (1711). As in other embodiments described herein, the resulting feature sets may be conveniently clustered and displayed by the Studies or taxonomy groups to which they belong.

After presenting the ranked list of feature sets as clustered by study as a result of the query, the process may be complete. However, in some embodiments, a Results window in a user interface allows the user to conduct further queries using the feature set provided as the query input or expand the results of the query. For example, as indicated at decision operation 1713, the system may allow users to expand results of a sequence-centric feature set. Thus, if decision 1711 is answered in the affirmative, the system may display all regions in the sequence-centric feature set that are mapped to the query gene, ranked by the weighted normalized rank in ascending order (1715). If answered in the negative, the user may navigate other search results, perform another query, etc.

Figure 18:
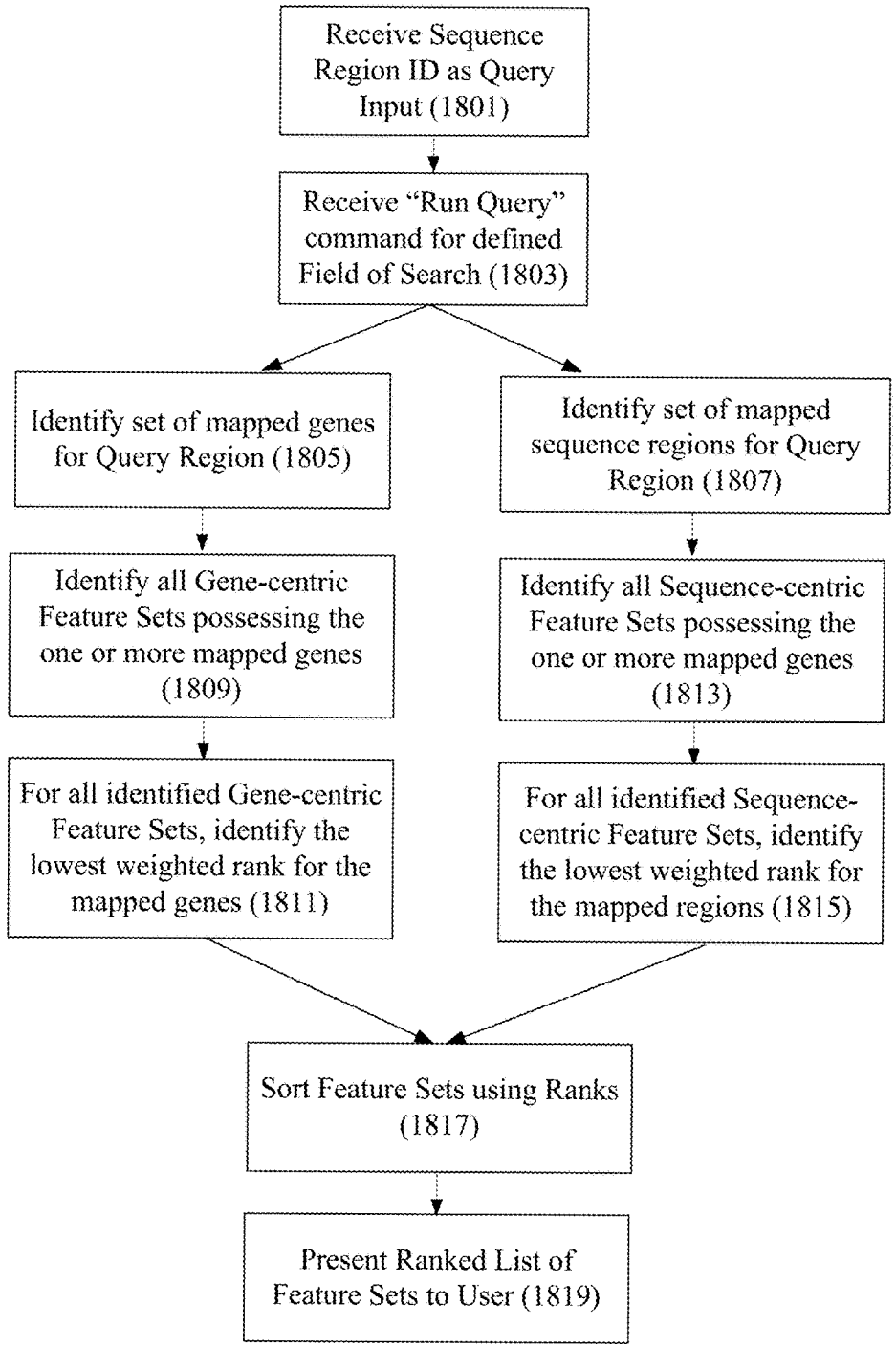
FIG. 18 is a flow diagram depicting operations in an example of querying a registered sequence region according to various embodiments.

Examples of other queries include sequence region queries. According to various embodiments, the queried sequence region may be a sequence region already registered within the system, or a user-defined sequence region. Examples of sequence regions that may be queried include haplotype blocks. FIG. 18 is a flow diagram depicting operations in an example of querying a registered sequence region according to certain embodiments. As illustrated, the process begins by receiving the identity of a sequence region (1801) followed by receiving a "Run Query" command (1803). For example, the query sequence region is input in the form of a Platform ID, name, feature ID, etc. Every registered sequence region in the knowledge base has a set of mapped genes and a set of mapped regions. These are identified (1805 and 1807). All gene-centric feature sets possessing the mapped genes are identified. (1809). For each identified gene-centric feature set, the lowest normalized weighted rank (NR/wi) of the mapped genes in the feature set is also identified to be used in ranking the feature sets in response to the query (1811). All sequence-centric feature sets containing the mapped regions are also identified (1813). For each identified sequence-centric feature set, the lowest normalized weighted rank (NR/vi) is also identified to be used in ranking the feature sets in response to the query (1815). Next the system sorts the identified feature sets by the normalized weighted ranks (1817). The next operation in the depicted query is presenting the user with a ranked list of feature sets, e.g., as clustered by Study (1819).

In certain embodiments, a query is input by the user specifying a chromosome and start and end coordinates. The system may check to see if the coordinates match any registered sequence regions. If so, the process continues to blocks 1805 and 1807 by identifying the set of mapped genes and set of mapped sequence regions. If the sequence region is not registered, then the process performs on the fly mapping of the sequence region to genes and other regions, e.g., as described above with respect to FIG. 5B, before proceeding to operations 1811 and 1815.

In another example, a sequence-centric feature set may be queried against genes. Here, the set of mapped genes for the sequence-centric feature set may be used to return query results. In another example, a SNP may be queried against SNP feature sets. According to various embodiments, the query may obtain all SNP feature sets possessing the SNP and return a result, with the SNP feature sets ranked according to a normalized rank of the SNP within each feature set.

Queries identifying a feature set as the query and a feature set or feature group as the field of search may involve the pre-computations of feature set correlations described above. For example, a sequence-centric feature set may be identified in a query. Depending on the field of search, the sequence-centric feature set may be compared to other feature sets using feature set to feature set scores and/or feature set to feature group scores. A list ranked using these scores may then be returned.

The above-described concept scoring may also be used for queries against concepts. For example, any of the following may be queried against concepts: genes, sequence regions, sequence-centric feature sets, gene-centric feature sets and feature groups. For all of these, concept scoring of sequence-centric feature sets, gene-centric feature sets, and SNP feature sets may be used. In certain embodiments, SNPs may be queried against concepts, with SNP feature sets only taken into account. Sequence-centric feature sets contribute to a concept score via the set of mapped genes or regions for the feature set, along with the normalized ranks for the mapping.

In one example of a query, a feature (e.g., SNP, other sequence region or gene) is received as query input. The query is run by determining the most relevant concepts to the feature by comparing the normalized ranks of the queried feature in all feature sets that contribute to a concept score across all (or at least a plurality of) concepts. As described above, concept scoring is based on determining the feature sets that contribute to a concept score, e.g., by having a qualifying basic category (see, e.g., block 1503 of FIG. 15 and 1603 of FIG. 16). Comparing the normalized ranks across all concepts to compute a feature-concept score according to certain embodiments is discussed above with respect to FIGS. 15 and 16. As discussed above, the weighted normalized ranks of a set of mapped genes and/or a set of mapped regions may be used. Note that if the feature—concept scores are pre-computed as described above with respect to FIG. 15 or FIG. 16, running the query may involve sorting the pre-computed concept scores feature or otherwise obtaining the top scoring concepts for the queried feature. The next operation in the depicted query involves presenting to the user the ranked list of concepts (i.e., the query result). As in other embodiments described herein, the resulting concepts may be conveniently displayed as grouped by category. For example, the results may show the top 10 concepts for each top-level category, and/or designated sub-category in an ontology. Concept-based queries identifying a feature set may be performed by comparing all feature set correlations for a queried feature sets and feature sets having a qualifying basic category across all concepts. This may involve sorting stored concept scores. Concept-based queries identifying a feature group may be performed by comparing all correlations for a queried feature groups and feature sets having a qualifying basic category across all concepts.

Figure 19:
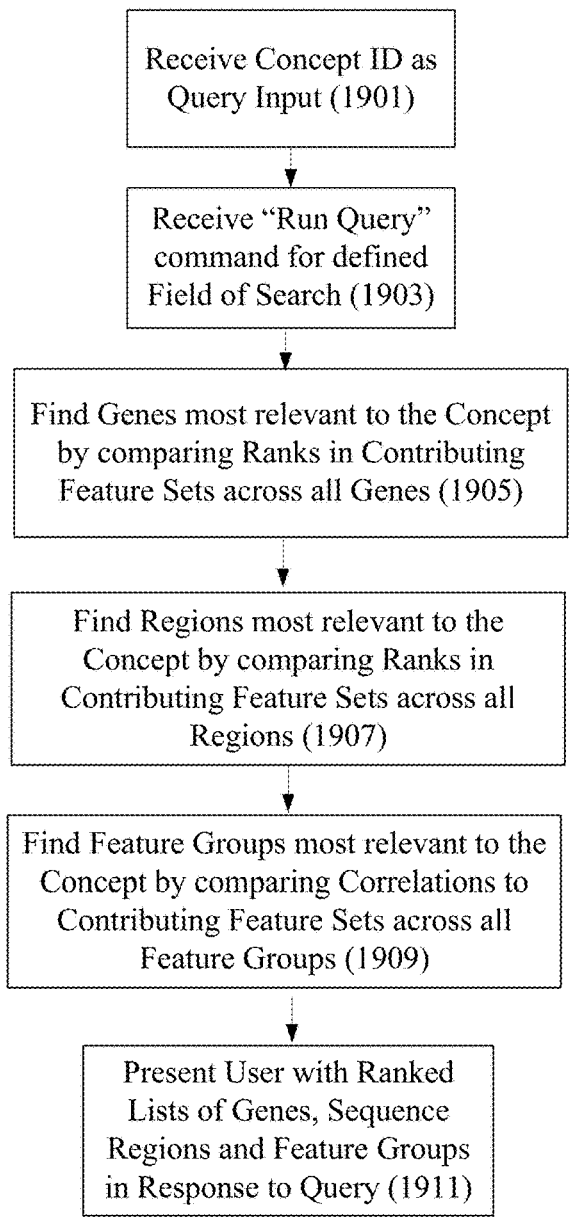
FIG. 19 is a flow diagram depicting operations in an example of querying a concept according to various embodiments

Queries identifying a concept may also be performed by to determine the features (e.g., genes or sequence regions) and/or feature groups most relevant to a concept. This may be done by comparing the ranks of all features in feature sets that contribute to a concept score across all concepts and/or comparing the feature group vs. feature sets correlations for all feature sets that contribute to a concept score across all feature groups. This is described in U.S. patent application Ser. No. 12/398,107, incorporated by reference. FIG. 19 is a flow diagram depicting operations in an example of querying a concept according to certain embodiments. As illustrated, the process begins by receiving a concept (1901) followed by receiving a "Run Query" command (1903). Next, the genes most relevant to the concept are found by comparing normalized ranks of feature sets that contribute to the queried concept across all genes (1905). As described above with regard to FIG. 15, the weighted ranks of the mapped genes of a sequence-centric feature set are used. The sequence regions most relevant to the queried concept are found by comparing the weighted normalized ranks of the feature sets that contribute to the queried concept across all sequence regions (1907). This may be done as described above with respect to FIG. 16. Then, the feature groups most relevant to the concept are found by comparing the feature group vs. feature set correlations for the feature sets that contribute to a concept score across all feature groups (1909). The user is then presented with a list or ranked genes, a list of ranked sequence regions and a list of ranked feature groups for the concept (1911), with the rankings indicating the relative relevance to the concept as determined in the previous operations.

The querying methodology and other aspects of the user navigation provide graphical representations of mappings and results, allowing users to visualize feature sets, as well view and sort them by statistics, allele calls or other information in the feature set. In certain embodiments, a user may expand or view a sequence-centric feature set (e.g., either on import, clicking on a displayed result, or by otherwise selecting the feature set). Each region's association with genes or known variations may be displayed graphically. For example, data from sequencing or methylation, protein-DNA binding, gene expression and other studies gene(s) mapped to a given sequence region may be displayed. In another example, for mutation sequencing and variation discovery studies a mapping to a known public variation (if it is available) may be displayed. Users may run queries for any region of interest within the dataset. Graphical representation for the type of mapping between a sequence region and public gene/variation will be available for quick visual interpretation of association.

In certain embodiments, graphical user interfaces for setting up queries and exploring query results that visually represent sequence regions and/or genes or other features based on genomic coordinates are provided. For example, a representation of a genome or genomic region is provided to enable users to define any arbitrary region of interest within, e.g., by clicking on or selecting a region of the representation. A user may also enter coordinates, e.g. in numerical form via a keypad. This will provide flexibility to explore any genomic region across all data available in the knowledge base. Known public variations (e.g. SNPs) may be searched and selected to use as query input.

Graphical representations of sequence-centric data may be provided. For example, if two datasets containing sequence regions are compared, exploring the details of their overlap will enable users to evaluate how different regions overlap with each other and with known genes. In addition, the extent of genomic overlap between two datasets may be presented, e.g., in a Venn diagram.

Systems to visualize sequence-centric data within the context of experimentally-derived genomic regions and variations may also be provided. For example, a user may explore a particular region of the genome and all associated information, especially within the context of a particular phenotype. A graphical representation of a given region of interest and associated gene, intron/exon, 5' and 3' UTR regions, and known variation context may be provided. Users will be able to explore the region of interest in multiple ways, e.g., 1) within the context of known genome structural elements and 2) within the context of regions identified in other experiments and pertaining to phenotype of interest. This enables users to explore hypotheses about possible mechanisms involved in association of a given region to a phenotype. Second, it enables them to explore all other orthogonal experimental data supporting and rejecting potential association of a given genomic region to a phenotype of interest. In addition, visual inspection of multiple regions related to a phenotype assist researchers in selecting the potential "consensus" region of interest to perform further experiments on.

Figure 20:
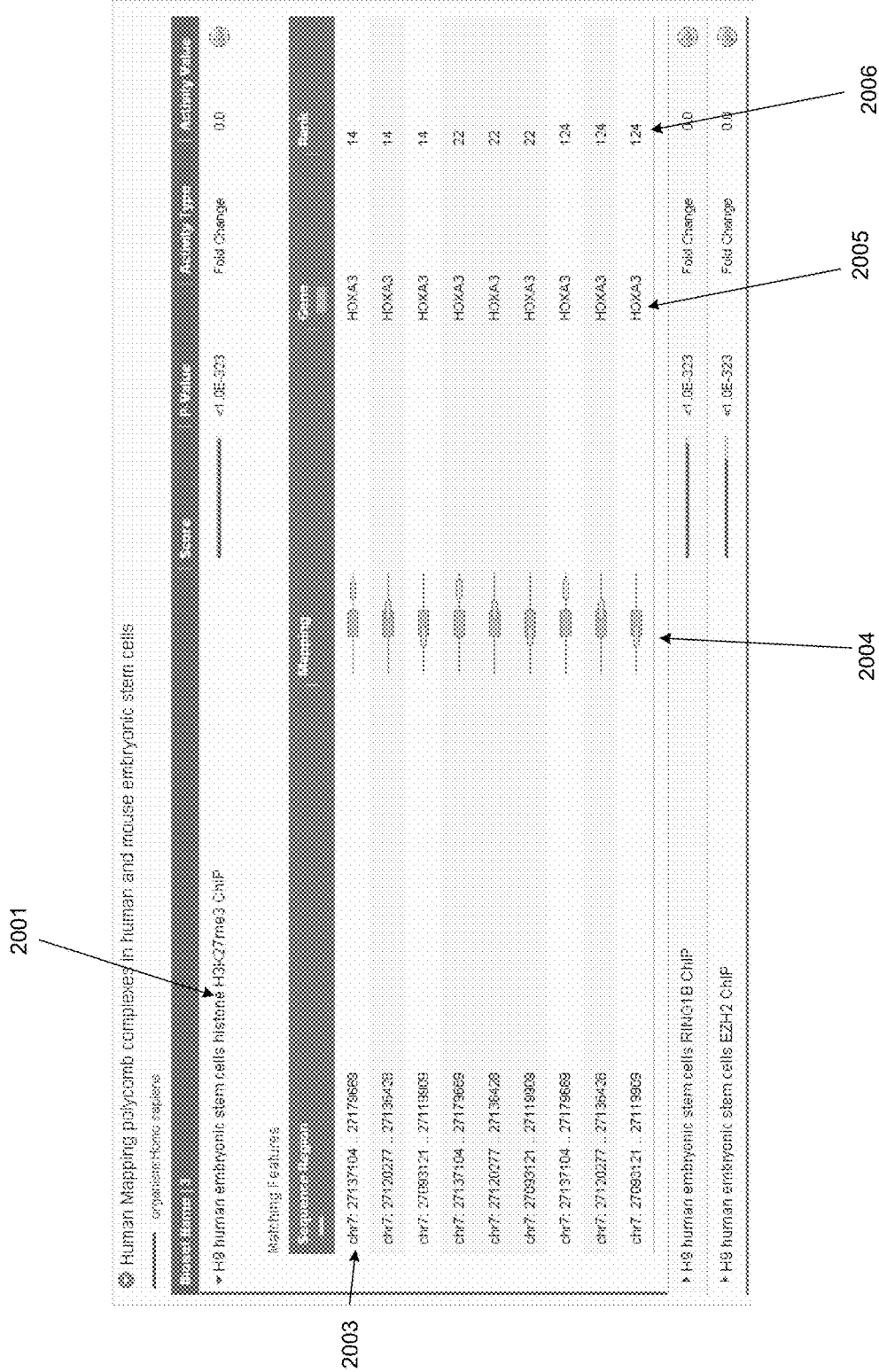
FIG. 20 presents a screenshot of a results window of the type that may be presented during a query as described above in which graphical representations of the association between sequence regions in a sequence-centric feature set and a gene is presented.

FIG. 20 presents a screenshot of a results window of the type that may be presented during a query as described above in which graphical representations of the association between sequence regions in a sequence-centric feature set and a gene is presented. As an example, a list of feature sets may be provided in a results window in response to a query identifying a feature set. A sequence-centric feature set in the results may be expanded as depicted in FIG. 20. Here, the feature set as identified as 2001 is expanded to show a list of sequence regions 2003 associated with the mapped-to feature 2005 (in this example, the HOXA3 gene) are shown. Graphical representations of the association of each sequence region 2001 to the gene are shown at 2004. Rank information is also presented at 2006.

5. Applications

Next generation sequencing technologies have the potential to revolutionize the field of genetics and help researchers to answer questions never before possible. Sequencing technologies developed by companies such as Roche (Roche 454), Illumina (Illumina/Solexa Genome Analyzer) and ABI (ABI SoLID) are able to produce millions of short sequence reads in a single run. Importantly, they are affordable enough to be used by researchers outside of major consortia. There are numerous applications of next-generation sequencing technologies that have been developed and that will be invented in the future. These will become commonly employed by most if not all research groups requiring nucleic acid analysis because of the increased quality, reduced price and simplicity of the protocols developed. Examples of sequence-centric data that may be integrated into the knowledge base described above include:

Mutation Discovery

The depth and precision of such advanced sequencing allows researchers to reliably and relatively cheaply perform targeted deep sequencing studies of genomic regions of interest. This can be used to validate or further results of genome-wide SNP association studies (GWAS), to perform mutation analysis and de novo SNP discovery in a variety of clinical applications, such as pharmacogenomics. A number of research studies have demonstrated the power of these newly developed sequencing approaches to detect mutations in selected or genome-wide exons. Thomas et al. demonstrated the ability to detect rare mutations in cancer cells with high sensitivity and reliability ("High-throughput oncogene mutation profiling in human cancer." *Nature genetics.* 2007 March 39(3): 347-51, incorporated by reference herein). In another study, Porreca et al. sequenced 10,000 exons using a massive parallel sequencing approach to detect genetic variants ("Multiplex amplification of large sets of human exons." *Nat Methods.* 2007 Nov. 4(11):931-6, incorporated by reference herein). Techniques for whole genome variant detection and discovery are being developed and present a much cheaper alternative than with the conventional approaches.

Applications of efficient and sensitive mutation and variant discoveries are numerous as illustrated by studies of somatic mutations in cancer, pharmacogenomic studies of variants of the P450 enzymes associated with sensitivity and metabolism of drugs, and many other research areas seeking to identify relationships between genetic variants and diverse phenotypes.

Transcriptome Analysis

Next generation sequencing technology can be also be applied to analyze expression levels of genome-wide transcripts in different cell types and under diverse conditions, to annotate genomes with new genes and transcripts and to discover and study abundance of small RNA molecules. The sequencing approach to study gene expression has significant advantages in that it is able to detect expression levels of known and novel splice variants, providing greater sensitivity of transcript detection and providing a potential to study gene expression in an allele-specific manner (Eveland et al., "Transcript profiling by 3'-untranslated region sequencing resolves expression of gene families." *Plant physiology.* 2008 January 146(1): 32-44, incorporated by reference herein).

Small non-coding RNA discovery and profiling is emerging as yet another important application of next-generation sequencing. Non-coding RNAs, such as miRNA have been shown to play a key role in post-translational regulation of gene expression during normal and disease development, such as cancer. See Morin et al., "Application of massively parallel sequencing to microRNA profiling and discovery in human embryonic stem cells." *Genome research.* 2008 April; 18(4): 610-2; and Lu et al., "MicroRNA expression profiles classify human cancers." *Nature.* 2005 Jun. 9; 435(7043): 834-8, both incorporated by reference herein.

Epigenetic DNA Modifications Analysis

The studies of epigenetic regulation of the genome are bound to greatly benefit from the next-generation sequencing technologies. Sequence-based studies of genome-wide protein-DNA interactions and histone modifications (ChIP-seq, Barski et al., "High-resolution profiling of histone methylations in the human genome." *Cell.* 2007 May 18; 129(4): 823-37, incorporated by reference herein) and methylation (Methyl-seq, Brunner et al., "Distinct DNA methylation patterns characterize differentiated human embryonic stem cells and developing human fetal liver." *Genome Res.* 2009 Mar. 9, incorporated by reference herein) have the promise to greatly benefit from the use of next-generation sequencing technologies. The unprecedented resolution and low false positives rate make it a powerful tool for epigenetic research quickly rivaling the traditional chip-based approaches which depend heavily of probe design and density of genome coverage. The studies of epigenetic patterns have wide-spread applications—from tissue specificity and development to disease progression.

Copy-Number Variation (CNV) Discovery

Copy number variations (CNVs) represent the most frequent structural variation in the human genome (Kidd et al., "Mapping and sequencing of structural variation from eight human genomes." *Nature.* 2008 May 1; 453(7191):56-64, incorporated by reference herein) varying in size from few thousand to several million base pairs. A number of recent studies have shown their importance in studies of inherited genetic diseases such as Crohn's disease and psoriasis, as well in protection against viral infections. Sequencing-based approach promises to accelerate the pace of CNV discoveries on a genome-wide level and integrate them into a mainstream biomedical research studies.

The sequence-centric framework described above enables researchers to integrate their sequence-centric based data sets, and correlate them with previous sequence-centric and gene-centric data to identify important connections between diverse phenotypes at the level of genomic variations, rearrangements, epigenetic modifications, gene and protein expression patterns.

A variety of applications enabled by next generation sequencing platforms have an underlying common theme despite their diversity—they produce results at the sequence level, independent of previously discovered genes, transcripts, structural variations and epigenetic patterns. The methods described above may be used to anchor this sequence-centric data using genomic coordinates to provide a way to link the data from the next generation sequencing platforms with gene-centric data derived from older approaches into a powerful new system of data analysis and interpretation.

The methods, systems and apparatuses for managing, correlating and mining sequence-centric results as well as gene-centric analysis results (sets of genes and proteins ranked by their activity) from high-throughput platforms. Pre-processed and curated data from the public domain (e.g., a curated and prepared by a knowledge base manager) is combined seamlessly with an individuals' and organizations' internal data to enable knowledge discovery across these global collections of data. As a result, researchers are able to perform two key functions: 1) run hypothesis generating queries across this entire collection of data and 2) import their own analysis results (e.g. gene or protein lists and associated statistics) and see their correlation with thousands of public and previous legacy studies. While correlating gene and protein expression signatures is an important step, integrating orthogonal types of data from next-gen sequencing studies as describes above provides greater power and a more comprehensive view of mechanisms regulating diverse biological conditions.

Sequence variation, genomic rearrangements, gene and protein expression and epigenetic regulation provide the foundation for studies of diverse conditions such as cancer, neurological and metabolic disorders, and drug response and normal development. The scientific framework required to bring this data together and mine it needs gene- and sequence-centric data to be integrated within one environment as described above. Gene-centric data such as microarray-based gene expression or proteomics studies connect all analysis results to genes (directly or via proteins). Genomic coordinates are used to integrate sequence-centric data and create mappings and connections across a diverse array of data sets. Connectivity between different data sets and a bridging between gene- and sequence-centric data can then be established to identify important genomic regions, genes, pathways and regulatory networks.

The sequence-centric data framework and knowledge base described above provide a foundation for exploring genomic bases for disease and variety of other phenotypes. For example, a concept query could allow a researcher to identify which genes and pathways are most significantly associated with glioblastoma progression based on the combined analysis of orthogonal data from gene expression, mutation, methylation and copy-number variation studies for glioblastoma. Associations between a sequence region of interest and specific or multiple types of cancer based on all sequence-centric data available in the public domain and within a researcher's organization may be identified by querying the region against a concept. The most important genomic regions associated with risk of developing Alzheimer's disease and its progression based on available next-generation mutation, methylation and microarray gene expression data may be similarly identified. A researcher may import a data set from a laboratory experiment and query it to find gene- and sequence-centric studies correlated to the data set of interest, as well as predominant phenotypes associated with these results. Mechanisms associated with a disease causing discovered mutations may be explored, e.g., by locating the mutations within a known protein-DNA binding region or a miRNA binding site discovered in previous experiments.

6. Computer Hardware

As should be apparent, certain embodiments of the invention employ processes acting under control of instructions and/or data stored in or transferred through one or more computer systems. Certain embodiments also relate to an apparatus for performing these operations. This apparatus may be specially designed and/or constructed for the required purposes, or it may be a general-purpose computer selectively configured by one or more computer programs and/or data structures stored in or otherwise made available to the computer. The processes presented herein are not inherently related to any particular computer or other apparatus. In particular, various general-purpose machines may be used with programs written in accordance with the teachings herein, or it may be more convenient to construct a more specialized apparatus to perform the required method steps. A particular structure for a variety of these machines is shown and described below.

In addition, certain embodiments relate to computer readable media or computer program products that include program instructions and/or data (including data structures) for performing various computer-implemented operations associated with at least the following tasks: (1) obtaining raw data from instrumentation, databases (private or public (e.g., NCBI, dbSNP), and other sources, (2) curating raw data to provide feature sets, (3) importing feature sets and other data to a repository such as database or knowledge base, (4) mapping features from imported data to pre-defined feature references in an index, (5) generating a pre-defined feature index, (6) generating correlations or other scoring between feature sets and feature sets and between feature sets and feature groups, (7) creating feature groups, (8) generating concept scores or other measures of concepts relevant to features, feature sets and feature groups, (9) determining authority levels to be assigned to a concept for every feature, feature set and feature group that is relevant to the concept, (10) filtering by data source, organism, authority level or other category, (11) receiving queries from users (including, optionally, query input content and/or query field of search limitations), (12) running queries using features, feature groups, feature sets, Studies, concepts, taxonomy groups, and the like, and (13) presenting query results to a user (optionally in a manner allowing the user to navigate through related content perform related queries). The invention also pertains to computational apparatus executing instructions to perform any or all of these tasks. It also pertains to computational apparatus including computer readable media encoded with instructions for performing such tasks.

Further the invention pertains to useful data structures stored on computer readable media. Such data structures include, for example, feature sets, feature groups, taxonomy hierarchies, feature indexes, score tables, and any of the other logical data groupings presented herein. Certain embodiments also provide functionality (e.g., code and processes) for storing any of the results (e.g., query results) or data structures generated as described herein. Such results or data structures are typically stored, at least temporarily, on a computer readable medium such as those presented in the following discussion. The results or data structures may also be output in any of various manners such as displaying, printing, and the like.

Examples of displays suitable for interfacing with a user in accordance with the invention include but are not limited to cathode ray tube displays, liquid crystal displays, plasma displays, touch screen displays, video projection displays, light-emitting diode and organic light-emitting diode displays, surface-conduction electron-emitter displays and the like. Examples of printers include toner-based printers, liquid inkjet printers, solid ink printers, dye-sublimation printers as well as inkless printers such as thermal printers. Printing may be to a tangible medium such as paper or transparencies.

Examples of tangible computer-readable media suitable for use computer program products and computational apparatus of this invention include, but are not limited to, magnetic media such as hard disks, floppy disks, and magnetic tape; optical media such as CD-ROM disks; magneto-optical media; semiconductor memory devices (e.g., flash memory), and hardware devices that are specially configured to store and perform program instructions, such as read-only memory devices (ROM) and random access memory (RAM) and sometimes application-specific integrated circuits (ASICs), programmable logic devices (PLDs) and signal transmission media for delivering computer-readable instructions, such as local area networks, wide area networks, and the Internet. The data and program instructions provided herein may also be embodied on a carrier wave or other transport medium (including electronic or optically conductive pathways). The data and program instructions of this invention may also be embodied on a carrier wave or other transport medium (e.g., optical lines, electrical lines, and/or airwaves).

Examples of program instructions include low-level code, such as that produced by a compiler, as well as higher-level code that may be executed by the computer using an interpreter. Further, the program instructions may be machine code, source code and/or any other code that directly or indirectly controls operation of a computing machine. The code may specify input, output, calculations, conditionals, branches, iterative loops, etc.

Figure 21:
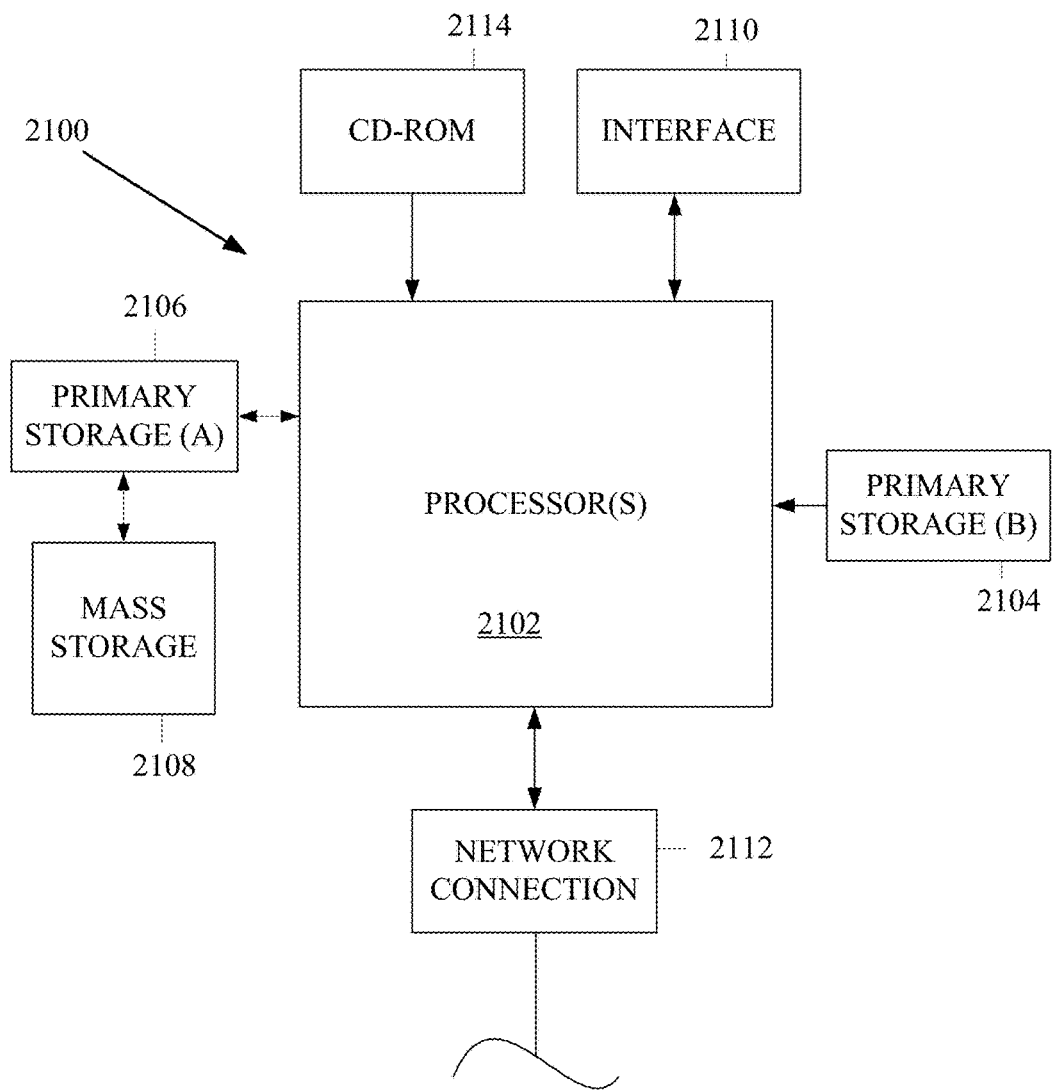
FIG. 21 illustrates, in simple block format, a typical computer system that, when appropriately configured or designed, can serve as a computational apparatus according to certain embodiments.

FIG. 21 illustrates, in simple block format, a typical computer system that, when appropriately configured or designed, can serve as a computational apparatus according to certain embodiments. The computer system 2100 includes any number of processors 2102 (also referred to as central processing units, or CPUs) that are coupled to storage devices including primary storage 2106 (typically a random access memory, or RAM), primary storage 2104 (typically a read only memory, or ROM). CPU 2102 may be of various types including microcontrollers and microprocessors such as programmable devices (e.g., CPLDs and FPGAs) and non-programmable devices such as gate array ASICs or general-purpose microprocessors. In the depicted embodiment, primary storage 2104 acts to transfer data and instructions uni-directionally to the CPU and primary storage 2106 is used typically to transfer data and instructions in a bi-directional manner. Both of these primary storage devices may include any suitable computer-readable media such as those described above. A mass storage device 2108 is also coupled bi-directionally to primary storage 2106 and provides additional data storage capacity and may include any of the computer-readable media described above. Mass storage device 2108 may be used to store programs, data and the like and is typically a secondary storage medium such as a hard disk. Frequently, such programs, data and the like are temporarily copied to primary memory 2106 for execution on CPU 2102. It will be appreciated that the information retained within the mass storage device 2108, may, in appropriate cases, be incorporated in standard fashion as part of primary storage 2104. A specific mass storage device such as a CD-ROM 2114 may also pass data uni-directionally to the CPU or primary storage.

CPU 2102 is also coupled to an interface 2110 that connects to one or more input/output devices such as such as video monitors, track balls, mice, keyboards, microphones, touch-sensitive displays, transducer card readers, magnetic or paper tape readers, tablets, styluses, voice or handwriting recognition peripherals, USB ports, or other well-known input devices such as, of course, other computers. Finally, CPU 2102 optionally may be coupled to an external device such as a database or a computer or telecommunications network using an external connection as shown generally at 2112. With such a connection, it is contemplated that the CPU might receive information from the network, or might output information to the network in the course of performing the method steps described herein.

In one embodiment, a system such as computer system 2100 is used as a special purpose data import, data correlation, and querying system capable of performing some or all of the tasks described herein. System 2100 may also serve as various other tools associated with Knowledge Bases and querying such as a data capture tool. Information and programs, including data files can be provided via a network connection 2112 for access or downloading by a researcher. Alternatively, such information, programs and files can be provided to the researcher on a storage device. In a specific embodiment, the computer system 2100 is directly coupled to a data acquisition system such as a microarray or high-throughput screening system that captures data from samples. Data from such systems are provided via interface 2110 for analysis by system 2100. Alternatively, the data processed by system 2100 are provided from a data storage source such as a database or other repository of relevant data. Once in apparatus 2100, a memory device such as primary storage 2106 or mass storage 2108 buffers or stores, at least temporarily, relevant data. The memory may also store various routines and/or programs for importing, analyzing and presenting the data, including importing Feature Sets, correlating Feature Sets with one another and with Feature Groups, generating and running queries, etc.

In certain embodiments user terminals may include any type of computer (e.g., desktop, laptop, tablet, etc.), media computing platforms (e.g., cable, satellite set top boxes, digital video recorders, etc.), handheld computing devices (e.g., PDAs, e-mail clients, etc.), cell phones or any other type of computing or communication platforms. A server system in communication with a user terminal may include a server device or decentralized server devices, and may include mainframe computers, mini computers, super computers, personal computers, or combinations thereof. A plurality of server systems may also be used without departing from the scope of the present invention. User terminals and a server system may communicate with each other through a network. The network may comprise, e.g., wired networks such as LANs (local area networks), WANs (wide area networks), MANs (metropolitan area networks), ISDNs (Intergrated Service Digital Networks), etc. as well as wireless networks such as wireless LANs, CDMA, Bluetooth, and satellite communication networks, etc. without limiting the scope of the present invention.

Although the foregoing invention has been described in some detail for purposes of clarity of understanding, it will be apparent that certain changes and modifications may be practiced within the scope of the invention. It should be noted that there are many alternative ways of implementing the processes and databases of the present invention. Accordingly, the present embodiments are to be considered as illustrative and not restrictive, and the invention is not to be limited to the details given herein.

What is claimed is:

1. A computer implemented method of conducting a query in a database comprising a plurality of sequence-centric feature sets and gene-centric feature sets, the sequence-centric feature sets comprising genomic sequence regions and associated statistics based on experiments on samples containing the genomic sequence regions and the gene-centric feature sets comprising genes and associated statistics based on experiments on samples containing the genes, the method comprising:
   (a) receiving, at a server computer comprising a processor and system memory, a query identifying a sequence-centric feature set or a gene-centric feature set, wherein the query is received from a user input to a query computer;
   (b) receiving, by the server computer, correlation scores indicating correlations between the queried sequence-centric feature set or the queried gene-centric feature set and two or more feature sets in the database, wherein each correlation score was calculated by an iterative rank-based process comprising:
      obtaining a first feature set in the database corresponding to the queried sequence-centric feature set or the queried gene-centric feature set,
      obtaining a second feature set in the database,
      mapping one or more features in the first feature set to one or more features in the second feature set to provide mapping information between the first and second feature sets,
      obtaining ranks of the one or more features in the first feature set and ranks of the one or more features in the second feature set, and
      calculating the correlation score using (i) the mapping information between the first and second feature sets, and (ii) the ranks of the one or more features in the first feature set and the ranks of the one or more features in the second feature set, the correlation score indicating a correlation between the first feature set and the second feature set;
   (c) calculating, by the server computer, feature set rankings for the two or more feature sets based on the correlation scores; and
   (d) outputting, based on the feature set rankings and by the server computer, a ranked list of the two or more feature sets to be presented to the user.

2. The computer implemented method of claim 1, wherein the plurality of sequence-centric feature sets and gene-centric feature sets in the database were obtained from a plurality of experiments, a plurality of platforms, or a plurality of organisms, and wherein at least some features of the feature sets in the database have different names and are associated with each other.

3. The computer implemented method of claim 1, wherein the correlation score comprises or is based on a p value.

4. A system comprising:
   a memory for storing a database comprising a plurality of feature sets, wherein each feature set of the plurality of features sets is either a sequence-centric feature sets or a gene-centric feature set, wherein each sequence-centric feature set comprises a plurality of sequence regions and associated statistics, and each gene-centric feature set comprises a plurality of genes and associated statistics; and
   one or more processors in communication with the memory, wherein the one or more processors are configured to:
      (a) receive a query identifying a sequence-centric feature set or a gene-centric feature set, wherein the query is received from a user input to a query computer;
      (b) receive, in response to said query, correlation scores indicating correlations between the queried sequence-centric feature set or the queried gene-centric feature set and two or more feature sets in the database, wherein each correlation score was calculated by an iterative rank-based process comprising:
         obtaining a first feature set in the database corresponding to the queried sequence-centric feature set or the queried gene-centric feature set,
         obtaining a second feature set in the database,
         mapping one or more features in the first feature set to one or more features in the second feature set to provide mapping information between the first and second feature sets,
         obtaining ranks of the one or more features in the first feature set and ranks of the one or more features in the second feature set, and
         calculating the correlation score using (i) the mapping information between the first and second feature sets, and (ii) the ranks of the one or more features in the first feature set and the ranks of the one or more features in the second feature set, the correlation score indicating a correlation between the first feature set and the second feature set;
      (c) calculate feature set rankings for the two or more feature sets based on the correlation scores; and
      (d) output, based on the feature set rankings, a ranked list of the two or more feature sets to be presented to the user.

5. The system of claim 4, wherein the plurality of feature sets in the database were obtained from a plurality of experiments, a plurality of platforms, or a plurality of organisms, and wherein at least some features of the feature sets in the database have different names and are associated with each other.

6. The system of claim 4, wherein the correlation score comprises or is based on a p-value.

7. The system of claim 6, wherein the p-value is obtained by a Fisher's Exact Test using the ranks of the one or more features in the first feature set and the ranks of the one or more features in the second feature set.

8. The system of claim 4, wherein the mapping is based on genomic coordinate, physical proximity, haplotype, function, or phenotype.

9. The system of claim 4, wherein the mapping comprises mapping the one or more features in the first feature set to one or more globally unique mapping identifiers, and/or mapping the one or more features in the second feature set to the one or more globally unique mapping identifiers.

10. The system of claim 4, wherein the ranks are obtained based on statistics associated with features of the first feature set and statistics associated with features of the second feature set.

11. The system of claim 4, the one or more processors are further configured to present the user with a graphical representation of associations between (i) features of a feature set in the ranked list of feature sets and (ii) other information in the database.

12. The system of claim 4, wherein the gene-centric feature sets in the database comprise microarray expression data.

13. The system of claim 4, wherein the sequence-centric feature sets in the database comprise one or more of methylated region data, genomic variation data, and epigenetic profiling data.

14. A computer program product comprising a non-transitory machine readable medium storing program code that, when executed by one or more processors of a computer system, causes the computer system to implement a method of querying a sequence-centric feature set or a gene-centric feature set against a database comprising a plurality of feature sets, wherein each feature set of the plurality of features sets is either a sequence-centric feature sets or a gene-centric feature set, each sequence-centric feature set comprises a plurality of sequence regions and associated statistics, and each gene-centric feature set comprises a plurality of genes and associated statistics, said program code comprising:
  (a) code for receiving a query identifying a sequence-centric feature set or a gene-centric feature set, wherein the query is received from a user input to a query computer;
  (b) code for correlating, in reply to said query, the queried sequence-centric feature set or the queried gene-centric feature set with two or more feature sets of the plurality of feature sets in the database, wherein the correlating comprises:
    obtaining a first feature set in the database corresponding to the queried sequence-centric feature set or the queried gene-centric feature set,
    obtaining a second feature set in the database,
    mapping one or more features in the first feature set to one or more features in the second feature set to provide mapping information between the first and second feature sets,
    obtaining ranks of the one or more features in the first feature set and ranks of the one or more features in the second feature set, and
    calculate the correlation score using (i) the mapping information between the first and second feature sets, and (ii) the ranks of the one or more features in the first feature set and the ranks of the one or more features in the second feature set, the correlation score indicating a correlation between the first feature set and the second feature set;
  (c) code for calculating feature set rankings for the two or more feature sets based on the correlation scores; and
  (d) code for outputting, based on the feature set rankings, a ranked list of the two or more feature sets to be presented to the user.

15. The computer implemented method of claim 3, wherein each p value is calculated by a Fisher's Exact Test using the ranks of the one or more features in the first feature set and the ranks of the one or more features in the second feature set.

16. The computer implemented method of claim 1, wherein the mapping comprises mapping the one or more features in the first feature set to one or more globally unique mapping identifiers, and/or mapping the one or more features in the second feature set to said one or more globally unique mapping identifiers.

17. The computer implemented method of claim 1, wherein at least some features of the feature sets have different names and are associated with each other.

18. The computer implemented method of claim 1, wherein the statistics associated with features are selected from a group consisting of: gene expression of said features, abundance of said features, responses of said features to a treatment or stimulus, and effects of said features on biological systems.

19. The method of claim 1, wherein the ranks of the one or more features in the first feature set and the ranks of the one or more features in the second feature set comprise normalized ranks.

* * * * *